United States Patent
Mayer et al.

(10) Patent No.: US 8,911,234 B2
(45) Date of Patent: Dec. 16, 2014

(54) IMPLANT THAT CAN BE IMPLANTED IN OSSEOUS TISSUE, METHOD FOR PRODUCING SAID IMPLANT AND CORRESPONDING IMPLANT

(75) Inventors: Jorg Mayer, Niederlenz (CH); Marcel Aeschlimann, Ligerz (CH); Laurent Torriani, Lamboing (CH); Christopher Rast, Biel (CH); Andrea Muller, Neftenbach (CH)

(73) Assignee: Woodwelding AG, Stansstad (CH)

( * ) Notice: Subject to any disclaimer, the term of this patent is extended or adjusted under 35 U.S.C. 154(b) by 1924 days.

(21) Appl. No.: 10/530,684

(22) PCT Filed: Jan. 28, 2005

(86) PCT No.: PCT/CH2005/000043
§ 371 (c)(1),
(2), (4) Date: Apr. 25, 2005

(87) PCT Pub. No.: WO2005/079696
PCT Pub. Date: Sep. 1, 2005

(65) Prior Publication Data
US 2006/0105295 A1    May 18, 2006

(30) Foreign Application Priority Data
Feb. 20, 2004 (CH) ........................ 287/04

(51) Int. Cl.
*A61C 13/12* (2006.01)
*A61F 2/28* (2006.01)
(Continued)

(52) U.S. Cl.
CPC ......... *A61B 17/68* (2013.01); *A61F 2002/4683* (2013.01); *A61C 8/0089* (2013.01); *A61B 2017/00955* (2013.01); *A61C 8/0016* (2013.01); *A61C 8/0012* (2013.01); *A61C 13/0004* (2013.01); *A61F 2002/30065* (2013.01); *A61C 8/0018* (2013.01); *A61F 2210/0071* (2013.01); *A61C 8/0045* (2013.01)
USPC .......................................... 433/173; 623/16.11

(58) Field of Classification Search
USPC .............. 433/172–177, 180; 606/72, 232, 67, 606/300, 329, 60; 411/490, 456, 451.3, 411/487, 82.1; 623/17.17, 23.26, 23.24, 623/23.31, 23.37, 16.11
See application file for complete search history.

(56) References Cited

U.S. PATENT DOCUMENTS 2,967,448 A * 1/1961 Hallock ...................... 411/490
3,067,740 A * 12/1962 Haboush .................. 623/22.15
(Continued)

FOREIGN PATENT DOCUMENTS

DE    26 55 086        6/1978
DE    37 23 643 A1    1/1989
(Continued)

OTHER PUBLICATIONS
English Language translation of WO/02069817, Apr. 30, 2003.*
(Continued)

*Primary Examiner* — Heidi M Eide
(74) *Attorney, Agent, or Firm* — Rankin, Hill & Clark LLP

(57) ABSTRACT

A bone implant (10) is implanted in a cavity parallel to an implant axis (l) and without substantial rotation. The implant includes, on an implant portion to be implanted, cutting edges (14), which do not extend in a common plane with the implant axis and are facing toward the distal end of the implant. The implant also includes surface ranges (16) of a material that is liquefiable by mechanical oscillations. The cutting edges (14) are dimensioned such that they are lodged in the cavity wall after implantation. For implantation, the implant is impinged with mechanical oscillations, resulting in the thermoplastic material being at least partially liquefied and pressed into unevennesses and pores of the cavity wall to form a form-fit and/or material-fit connection between implant (10) and cavity wall, when re-solidified. The cutting edges (14) anchor the implant in the cavity wall.

24 Claims, 11 Drawing Sheets

(51) Int. Cl.
*A61B 17/68* (2006.01)
*A61F 2/46* (2006.01)
*A61C 8/00* (2006.01)
*A61B 17/00* (2006.01)
*A61C 13/00* (2006.01)
*A61F 2/30* (2006.01)

(56) References Cited

U.S. PATENT DOCUMENTS

| | | | |
|---|---|---|---|
| 3,672,058 A * | 6/1972 | Nikoghossian | 433/174 |
| 4,032,803 A | 6/1977 | Durr et al. | |
| 4,248,232 A | 2/1981 | Engelbrecht et al. | |
| 4,261,351 A * | 4/1981 | Scherfel | 606/62 |
| 4,547,157 A | 10/1985 | Driskell | |
| 4,687,443 A * | 8/1987 | Driskell | 433/173 |
| 4,846,839 A * | 7/1989 | Noiles | 623/23.46 |
| 5,004,422 A | 4/1991 | Propper | |
| 5,007,932 A * | 4/1991 | Bekki et al. | 623/23.39 |
| 5,019,083 A | 5/1991 | Klapper et al. | |
| 5,088,926 A * | 2/1992 | Lang | 433/173 |
| 5,163,960 A | 11/1992 | Bonutti | |
| 5,167,619 A | 12/1992 | Wuchinich | |
| 5,171,148 A | 12/1992 | Wasserman et al. | |
| 5,199,873 A * | 4/1993 | Schulte et al. | 433/174 |
| 5,383,935 A * | 1/1995 | Shirkhanzadeh | 623/23.49 |
| 5,413,578 A | 5/1995 | Zahedi | |
| 5,426,341 A | 6/1995 | Bory et al. | |
| 5,562,450 A | 10/1996 | Gieloff et al. | |
| 5,593,425 A | 1/1997 | Bonutti et al. | |
| 5,593,446 A * | 1/1997 | Kuoni | 623/23.44 |
| 5,665,091 A * | 9/1997 | Noble et al. | 606/85 |
| 5,709,823 A | 1/1998 | Hahn | |
| 5,735,875 A | 4/1998 | Bonutti et al. | |
| 5,752,831 A | 5/1998 | Padros-Fradera | |
| 5,871,514 A | 2/1999 | Wiklund et al. | |
| 5,871,515 A | 2/1999 | Wiklund et al. | |
| 5,897,578 A | 4/1999 | Wiklund et al. | |
| 5,919,215 A | 7/1999 | Wiklund et al. | |
| 5,941,901 A | 8/1999 | Egan | |
| 5,964,764 A | 10/1999 | West, Jr. et al. | |
| 5,993,458 A | 11/1999 | Vaitekunas et al. | |
| 5,993,477 A | 11/1999 | Vaitekunas et al. | |
| 6,007,539 A | 12/1999 | Kirsch et al. | |
| 6,039,568 A | 3/2000 | Hinds | |
| 6,056,751 A | 5/2000 | Fenton, Jr. | |
| 6,059,817 A | 5/2000 | Bonutti et al. | |
| 6,080,161 A | 6/2000 | Eaves, III et al. | |
| 6,099,313 A | 8/2000 | Durken et al. | |
| 6,132,214 A | 10/2000 | Suhonen et al. | |
| 6,139,320 A | 10/2000 | Hahn | |
| 6,141,874 A | 11/2000 | Olsen | |
| 6,142,782 A * | 11/2000 | Lazarof | 433/174 |
| 6,193,516 B1 | 2/2001 | Story | |
| 6,224,373 B1 | 5/2001 | Lee et al. | |
| 6,273,717 B1 | 8/2001 | Hahn et al. | |
| 6,332,885 B1 | 12/2001 | Martella | |
| 6,545,390 B1 | 4/2003 | Hahn et al. | |
| 6,592,609 B1 | 7/2003 | Bonutti | |
| 6,635,073 B2 | 10/2003 | Bonutti | |
| 6,916,177 B2 * | 7/2005 | Lin et al. | 433/173 |
| 7,008,226 B2 | 3/2006 | Mayer et al. | |
| 2002/0044753 A1 | 4/2002 | Nagayama et al. | |
| 2002/0077662 A1 | 6/2002 | Bonutti et al. | |
| 2003/0118518 A1 | 6/2003 | Hahn et al. | |
| 2004/0053196 A1 | 3/2004 | Mayer et al. | |
| 2008/0275500 A1 | 11/2008 | Aeschlimann et al. | |

FOREIGN PATENT DOCUMENTS

| | | |
|---|---|---|
| DE | 39 19 274 C1 | 7/1990 |
| DE | 90 12 044.2 | 12/1990 |
| DE | G 90 12 548.7 | 1/1991 |
| DE | 41 00 636 A1 | 7/1992 |
| DE | 42 09 191 A1 | 5/1993 |
| DE | 93 17 757.7 | 3/1994 |
| DE | 196 44 333 A1 | 4/1998 |
| DE | 197 35 103 A1 | 10/1998 |
| DE | 199 16 158 A1 | 10/2000 |
| DE | 199 16 160 A1 | 10/2000 |
| DE | 201 13 692 U1 | 12/2001 |
| EP | 0 451 932 A1 | 10/1991 |
| EP | 0 534 078 A1 | 3/1993 |
| EP | 0 806 192 A2 | 11/1997 |
| EP | 1 044 655 A1 | 10/2000 |
| EP | 1 044 656 A1 | 10/2000 |
| GB | 2 324 470 A | 10/1998 |

OTHER PUBLICATIONS

Patent Abstracts of Japan, Bone Fixation Pin and Manufacture Thereof, Dec. 8, 1998.
WO 02/38070 A1, (Medical, Medical, Preferably Dental, Handpiece for Treating Tissue With Preferably High Frequency Mechanical Vibrations, May 16, 2002.
WO 02/087459 A2, Handpiece for Linear Actuation of a Tool, Preferably a Dental Tool, Nov. 7, 2002.
WO 94/27558, Ceraminc Dental Restorations, Dental Prostheses, Medical Implants and Moulded Bodies, and Process for Producing Same, Dec. 8, 1994.
WO 91/03211, Process for Producing a Tooth Crown With the Aid of Two Sonotrodes, Device Workpieces Using a Sonotrode . . . , Mar. 21, 1991.
WO 88/03391, Intraalveolar Implant, May 19, 1998.
WO 96/37163, Process and Device for the Computer-Assisted Restoration of Teeth, Nov. 28, 1996.
Leitgeb, N. et al.; "Die Stabilitat der Ultraschall-Osteosynthese (Stability of Ultrasound Osteosynthesis)"; Biomed. Technik, 30 (1985); pp. 44-48.
TH. Muller, Von et al.; "Grundlagenuntersuchungen zur Ultraschallchirurgie"; Z. Exper. Chirurg 15 (1982); pp. 244-250.
Forssell, H. et al.; "Experimental Osteosynthesis with Liquid Ethyl Cyanacrylate Polymerized with Ultrasound"; Traumatic Surgery (1984) 103; pp. 278-283.
Picht, U. et al.; "Sagen and Schweissen mit Ultraschall"; Z. Orthop. 115 (1977); pp. 82-89.
Kuhne, W. et al.; Heilungsvorgange an ultraschallgeschweissten Knochenfrakturen des Kaninchens (Healing processes of ultrasonically welded bone fractures in rabbits); Exp. Path. 16 (1978); pp. 102-108.
Brug, E et al.; "Die Ultraschallverschweissung von Knochen"; Chirurg 47 (1976); pp. 555-558.
WO 02/069817 A1, "Implants, Device and Method for Joining Tissue Parts"; Publication Date: Sep. 12, 2002.
WO 98/47440 A1, "Dental Implant, Method for Making a Cavity Intended to Receive Said Implant, and Instrument Needed for the Implantation"; Publication Date: Oct. 29, 1998.

* cited by examiner

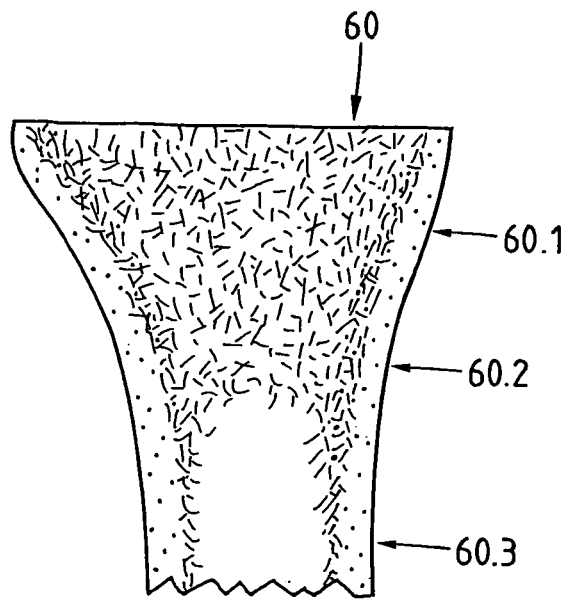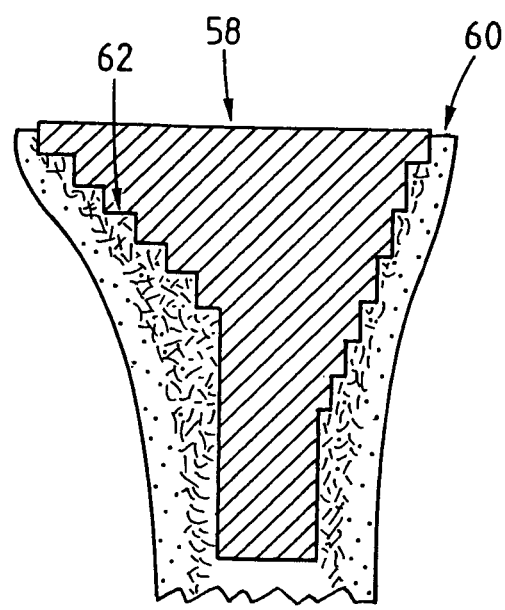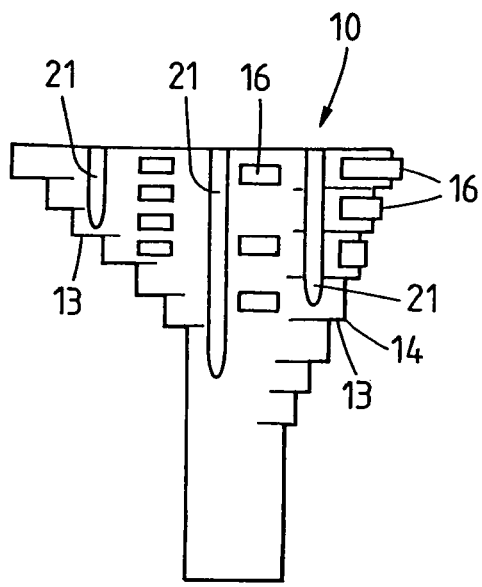
Fig. 23A  Fig. 23B
Fig. 23C

IMPLANT THAT CAN BE IMPLANTED IN OSSEOUS TISSUE, METHOD FOR PRODUCING SAID IMPLANT AND CORRESPONDING IMPLANT

BACKGROUND OF THE INVENTION

1. Field of the Invention

The invention lies in the field of medical technology and concerns an implant to be implanted in bone tissue, which implant may be a standardized one being implanted in a cavity especially created or adjusted for the purpose, or an individual implant being implanted in an individual bone cavity (e.g. dental implant, joint implant, or an implant to fill a bone defect). The invention further concerns methods for producing and implanting the implant.

2. Description of Related Art

Implants to be implanted in bone tissue are usually implanted in bone cavities, which are especially created for the purpose (e.g. bore or stepped bore) or which are caused by other circumstances, e.g. trauma or degenerative disease. According to state-of-the-art technology, such implants are either fitted into the cavity by means of cement placed around the implant, or the shape of the implant is adapted to the cavity so accurately that, after implantation, as much as possible of the functionally essential implant surface is in direct contact with the bone tissue. For an individual implant this means that the shape of the implant is irregular, in particular it is an irregular cone without consistently round cross sections and/or without a straight axis.

Dental implants to be implanted in the jaw bone for replacing a natural tooth root and for supporting e.g. an artificial crown, an abutment, a bridge, or a set of dentures, are known as standardized implants to be implanted in specially produced or at least correspondingly adapted cavities, and also as individual implants adjusted to the shape of an individual root or alveolus.

Standardized dental implants to be implanted in specially created bores are cylindrical or slightly conical, in essence rotationally symmetrical pins, mostly screws. They are available on the market in various sizes and shapes, from which the dental surgeon chooses the implant most suited to a specific case. Implantation of such a dental implant is generally not possible until the cavity resulting from the extraction of the natural root to be substituted has filled with regenerated bone tissue, i.e. until after a waiting period of 3 to 6 months following the extraction. Usually the screwed implant is not loaded immediately after implantation, as the risk is too high that the stress would cause the implant to move too much in relation to the bone tissue. This would prevent a successful integration of the implant in the bone tissue (osseointegration). In a vast majority of cases therefore, a part protruding from the jaw (crown, bridge, etc.) is not mounted on the implant until after a further waiting period of 3 to 6 months, i.e. not until the implant is fully integrated in the bone tissue and relative movements between the implant and the bone tissue caused by normal loading no longer exceed a physiologically tolerable range.

Experience shows that screw-shaped dental implants which are fully integrated in the jawbone have a stability which is sufficient for normal load situations and remains unchanged over a long time. Among other things, this is due to the implant being firmly anchored laterally in the bone tissue by the thread, which reduces shearing relative to the bone tissue and prevents undesirable pressure on the base of the alveolus.

It is well known that bone tissue tends to recede in an undesirable manner during the waiting periods mentioned above, in which the dental implant or jawbone is locally not loaded. It is also known that relative movements between implant and bone tissue which do not exceed a physiologically tolerable range would stimulate bone regeneration and therefore osseointegration of the implant. For these reasons there are a number of attempts to find ways and means for reducing or even eliminating the waiting periods.

In order to reduce the first waiting period, i.e. the time it takes the cavity caused by the extraction of the natural root to fill with regenerated bone tissue, as well as to be able to exploit the advantage of the denser bone layer (alveolar bone) surrounding the natural cavity (alveolus) as a supporting element, it is suggested to shape the implant not rotationally symmetrical and round like a screw, but essentially corresponding with the shape of the natural root to be substituted (individual implant). Such an implant can be implanted in the existing cavity (natural alveolus) immediately or shortly after the extraction of the natural root.

However, since under natural conditions there is a fibrous support membrane between the dental root and the alveolar wall, an implant which is an exact copy of the natural root (e.g. produced by negative-positive casting method) does not sit tightly in the alveolus. This has a negative effect on osseointegration during the second waiting period such that a kind of connective tissue forms in the gap between the alveolar wall and the implant, which connective tissue prevents osseointegration at least locally and is not able to lend the implant sufficient stability.

In order to improve the implant stability for the osseointegration phase (second waiting period) and therewith the starting conditions for successful osseointegration, it is suggested in U.S. Pat. No. 5,562,450 (Gieloff et al.) and WO-88/03391 (Lundgren) to oversize the implant compared to the natural root, i.e. to give it slightly larger cross sections, and structure the implant surface coming into contact with the bone, in particular with depressions (honeycomb structures, structures with undercuts). The said implants are e.g. produced by contact-less measuring of the natural root after its extraction or of the alveolus, by processing the measuring data in a CAD-system and by fashioning the implant from an appropriate blank in a CAM-system, based on the processed measuring data, by milling, grinding, electronic erosion, etc.

Due to the 'press fit' of such oversized dental implants sit considerably tighter in the alveolus than exact replica of natural roots. However, experience shows that the alveolar wall counteracts the applied press-fit forces within a short time by modification processes and mechanical relaxation. Thus the implant is no longer stabilized by 'press-fit' but sits loosely in the alveolus once more, so that conditions for osseointegration are not optimal in spite of the improved primary stability immediately after the implantation. It is also evident that even after the osseointegration phase (second waiting period) these implants tend to loose their grip in the jawbone when loaded. As reported by R.-J. Kohal et al. (published in Dent Sci (2) 7: 11) at the 52nd annual conference of the German Society for Dental Prosthetics and Material Science (DGZPW) in May 2003, the jawbone regresses a great deal in the area of such implants during the osseointegration phase and under subsequent loading, and the implants may even get completely loose.

The aforementioned findings can be explained by, among other things, the large-surface contact between implant and bone tissue which is subjected to intense modification resulting from surgery (tooth extraction) so that the stresses induced in the bone are only very slight. This applies not only to dental implants but generally to implants that are to be implanted into bone cavities. Although the surface geometries can raise the tension very locally via the 'press fit', the concerned volume however, appears to be too small for effectively reach a mechanically induced stimulation of bone regeneration. The force of pressure upon the implant created by load (chewing movement) lead mainly to shearing forces in the cavity wall. Furthermore, the form-fit between implant and cavity wall can hardly give enough stability against torsional forces. Due to the lack of sufficient rotational stability, dislocations can occur in the region of the regenerating bone, which dislocations prevent successful osseointegration. These problems have been discussed in depth, particularly in connection with hip joint prostheses. For dental implants transfer of the axial stress to the lateral alveolar wall is only possible to a limited degree, due to the steepness of this wall. This means that the stress shifts from the proximal part of the alveolus (natural tooth) toward the distal part of the alveolus (implant), possibly resulting in excessive loading of the alveolar base, which, being the point of exit for the blood vessels and nerves, is of course not fully ossified immediately after extraction. Pressure necrosis and other problems induced by misdirected load may be the consequences. In the design of conventional screw implants a great deal of attention is paid to these problems, even though in this case the alveolus is normally completely ossified.

To sum up, it can be said that of the known bone implants to be implanted without cement, the screw-shaped implants are preferable to all other forms with regard to stability, but that they often cannot be used due to the inevitable geometrical preconditions necessary for their application, or at least not without suffering other disadvantages. Something similar applies to many other implants to be implanted in bone tissue.

SUMMARY OF THE INVENTION

Thus it is the object of the invention to create an implant (individual or standardized) to be implanted in bone tissue as well as methods of production and implantation thereof. Once fully integrated in the bone tissue, the stability of the implant according to the invention is to at least match the stability of a screw-shaped implant screwed into a corresponding bore. However, primary stability of the implant according to the invention (immediately following implantation) is to be significantly better (in particular against torsional loading) than the primary stability of the screw-shaped implant. Furthermore, the implant according to the invention is to be significantly less geometrically limited than the screw-shaped implant. All the same it is to be possible to implant the implant according to the invention with per se known methods and to produce the implant with per se known procedures.

This object is achieved by the implant and the methods as defined in the corresponding claims.

The implant according to the invention is implanted essentially parallel to an implant axis (i.e. without substantial rotation) and it comprises a distal end area facing forward in implantation direction and a proximal end area located opposite to the distal end area along the implant axis. In an implanted state, the proximal end area is positioned in the region of the bone surface or possibly protrudes from the bone. The implant surfaces between the distal and the proximal end areas, which surfaces are at least partially brought into contact with the bone tissue on implantation, are equipped with chip-forming cutting edges. These cutting edges do not extend in a common plane with the implant axis, i.e., on implantation, they are not moved in the bone tissue parallel to their length but essentially at right angles it, and they are facing toward the distal end area. In addition the implant comprises a material which is liquefiable by mechanical vibration, e.g. a thermoplast, which material is situated in surface areas without cutting edges or is positioned or positionable in a hollow space within the implant, wherein the hollow space is connected to the surface areas without cutting edges by openings.

The implant according to the invention is inserted into the bone cavity substantially in the direction of the implant axis, i.e. without substantial rotation, wherein the cutting edges cut into the bone surface. Simultaneously with the insertion of the implant into the bone cavity the implant is impinged with mechanical vibration. This causes the liquefiable material, in this case advantageously a thermoplastic material, to liquefy at points of contact with the bone material and to be pressed into unevennesses and pores, or into structures in the cavity wall specifically fashioned for this purpose, thus being brought into intensive contact with the bone surface. Having set again, the liquefiable material forms a link between the implant and the bone tissue interlocking the two by form fit and possibly material fit.

In the case of the liquefiable material being positioned in a hollow space of the implant, the mechanical vibration is advantageously not applied to the implant until the implant is positioned in the cavity and then only to the liquefiable material. In this case, the liquefiable material may be a thermoplastic material or a thixotropic, particulate, hydraulic or polymeric cement, as also used in orthopaedics for anchoring implants or e.g. for the infiltration of diseased collapsed vertebrae.

The implant according to the invention is stabilized in the cavity immediately after the implantation by its connection with the bone tissue through the liquefiable material, wherein this stabilization is effective against pressure and tension (e.g. parallel to the implant axis) as well as against torsional loading. The cutting edges cutting into the bone tissue during implantation also contribute to the anchoring of the implant. The anchoring by both the liquefiable material as well as the cutting edges is particularly effective on the lateral walls of the cavity, such that the load on the cavity base is reduced or eliminated, which is particularly important for dental implants. All named effects lend the implant according to the invention a primary stability, which is in most cases sufficient to withstand loading immediately after implantation. The connective structures of thermoplastic material possess a lesser elastic modulus than the bone matrix, and in particular the implant itself, and their ability to creep make them particularly advantageous for absorbing shocks and for reducing excessive stress. Their elasticity permits small relative movements between implant and bone tissue, which promote osseointegration by stimulating the bone tissue particularly in the area of the cutting edges. At the same time these connections prevent major displacements between implant and bone tissue, which would lead to the disruption of the osseointegration process.

Because the implant according to the invention is implanted essentially without rotation (in particular without rotation greater than 360°), it is possible and advantageous to fashion the implant in such a manner that its shape contributes to its stability against torsional forces in the cavity. As is yet to be shown, it is nevertheless possible to design the implant according to the invention to be suitable for implantation in a cavity with a round cross section (bore or stepped bore).

If the implant according to the invention is an individual implant, it will in most cases have the shape of an irregular (not round) cone, i.e. it will taper towards its distal end, and in the case of a dental implant, it will have a shape being essentially adapted to the shape of a natural dental root. Such an individual dental implant according to the invention can, like known dental implants copying the natural root, be implanted immediately after extraction of the natural root. However, contrary to known individual dental implants, also called tooth replica, the implant according to the invention remains stable during the osseointegration phase and for a long time afterwards, as is the case for screw-shaped dental implants. The same applies to individual joint prosthesis implants according to the invention and such implants for the repair of individual bone defects.

If the implant according to the invention (e.g. dental implant) tapers towards the distal end, the cutting edges are designed as outer edges of step-shaped reductions in cross section (steps). In this case also, the cutting edges are dimensioned in relation to the cavity in such a manner that on implantation they cut into the cavity wall and remain at least partly lodged therein after implantation.

The cutting edges, or the steps equipped with cutting edges, extend wholly or partly around the implant, essentially perpendicular or at an angle to the implant axis, and they have a wedge angle of less than 90° (see FIG. 5). In addition to the cutting edges an implant designed as a cone may also comprise step-shaped reductions in cross section (steps) without a cutting action (wedge angle 90° or more).

For steps without cutting edge and/or for steps being relatively deep, it is advantageous to create appropriate shoulders in the cavity prior to implantation, e.g. with the aid of a tool adapted in shape to the implant. Whether the method with or without pre-shaping of shoulders in the cavity is chosen, depends in particular on the condition of the bone tissue on hand, but also on the surgeon and patient. Pre-shaping of shoulders (their depths being about equal to the depths of the corresponding implant steps) reduces the mechanical stress on the bone tissue during implantation, rendering this method particularly suitable for older patients with inferior bone quality.

Once implanted, the cutting edges of the implant according to the invention are lodged in the bone tissue of the cavity wall, similarly to the threads of a screw-shaped implant, and thus form lateral supports in the bone tissue, i.e. points where pressure forces acting on the implant are coupled into the bone tissue from lateral implant areas, and in fact more orthogonally than is possible through a conical or cylindrical, essentially smooth implant surface without cutting edges and steps. These lateral supports represent specifically loaded points where bone regeneration is stimulated.

In addition to the structures described above, the implant according to the invention may also comprise furrowing or self-tapping structures extending in a common plane with the implant axis, i.e. essentially in the implanting direction. These structures penetrate the cavity wall and lend the implant primary stability particularly with regard to torsional forces. The implant according to the invention may also comprise a cutting collar in the proximal area, further stabilising the implant in the surface of the cortical bone.

The surface areas of the cutting edges on an implant according to the invention consist of a material which is suitable for cutting into bone material, and which does not liquefy under the conditions of the implantation. They consist e.g. of titanium, of a titanium alloy, of zirconia, or of another suitable metallic or ceramic material, or of an appropriately reinforced polymer.

The liquefiable material to be applied in the implant according to the invention is advantageously biologically resorbable. The liquefiable material does not extend across the surface areas with the cutting edges, where the implant surface is biologically compatible, i.e. of bone-friendly and advantageously osseointegrative character. On these surface areas osseointegration of the implant can begin immediately after implantation and can successively relieve the anchoring by the resorbable thermoplastic material. It is possible also to use a non-resorbable thermoplastic material in such a manner that its anchoring in the bone tissue permanently complements or even replaces the anchoring by osseointegration. In this case a more extensive coverage of the implant surface with the polymer may be useful.

Biologically resorbable liquefiable materials suitable for the individual implant according to the invention are: thermoplastic polymers based on lactic and/or gluconic acid (PLA, PLLA, PGA, PLGA etc) or polyhydroxy alkanoates (PHA), polycaprolactones (PCL), polysaccharides, polydioxanones (PD), polyanhydrides, polypeptides, trimethyl-carbonates (TMC), or corresponding copolymers, or mixed polymers, or composites containing said polymers. Suitable non-resorbable thermoplastic materials are e.g. polyolefines (e.g. polyethylene), polyacrylates, polymethacrylates, polycarbonates, polyamides, polyesters, polyurethanes, polysulfones, liquid-crystal-polymers (LCPs), polyacetals, halogenated polymers, in particular halogenated polyolefines, polyphenylene sulphones, polysulfones, polyethers, or corresponding copolymers and mixed polymers or composites containing said polymers.

Particularly suitable as resorbable liquefiable materials are: poly-LDL-lactide (e.g. available from Böhringer under the trade name RESOMER LR708™) or poly-DL-lactide (e.g. available from Böhringer under the trade name RESOMER R208™); as non-resorbable liquefiable material: polyamide 11 or polyamide 12.

The most important advantages of the implant according to the invention are the following:

As the implant according to the invention can be implanted essentially without rotation around the implant axis, it can be adapted to fit an existing cavity, e.g. an alveolus, in which it can be implanted essentially immediately after extraction of the natural root. For the patient this means no waiting period between extraction and implantation. Furthermore, there is no need for elaborate measures for the exact alignment of the dental implant, and further parts (abutment, crown, etc.).

In the case of a dental implant adapted to the natural root, the alveolar wall largely remains in tact during implantation as an area with a densified bone structure and can support the implant better than less dense bone tissue further removed from the alveolus.

As the implant is sufficiently stabilized due to its anchoring by the liquefiable material, due to the penetration of the cutting edges into the bone material, and due to its shape preventing rotation in the cavity, it may be loaded immediately after implantation.

As a dental implant according to the invention can be loaded in essence immediately after implantation, it can be designed as an entire tooth with root and crown in one piece. Further procedures for complementing the implant in the mouth of the patient are not necessary.

As the implant is laterally supported in the cavity wall by the cutting edges, pressure forces upon the implant are coupled locally into the bone tissue, lending the implant a long-term stability equal to the long-term stability of a screw-shaped implant.

As the lateral support of the implant in the bone tissue of the cavity wall prevents, or at least relevantly reduces, its impact on the base of the cavity, complications on the cavity base are avoided, which is particularly important for dental implants where the base of the alveolus is not equipped for major loading.

Due to loading of the implant immediately after implantation there is no bone regression caused by lack of stress.

Stress induced relative movements between implant and bone tissue are reduced to a physiological range by the anchoring of the implant through the liquefiable material, and thus osseointegration is not only uninhibited but in fact encouraged.

The use of a non-resorbable liquefiable material enables a strong long-term anchoring of the implant even in bone tissue that is weak or little able to regenerate due to illness or old age.

BRIEF DESCRIPTION OF THE DRAWINGS

Various exemplary embodiments of the implant according to the invention, as well as the production and implantation thereof are described in detail in connection with the following Figs., wherein:

FIG. 23A to 23C illustrate implantation of a joint prosthesis designed as an implant according to the invention;

In all Figs. identical elements are denominated by identical reference numbers.

DETAILED DESCRIPTION OF THE PREFERRED EMBODIMENTS

Figure 1:
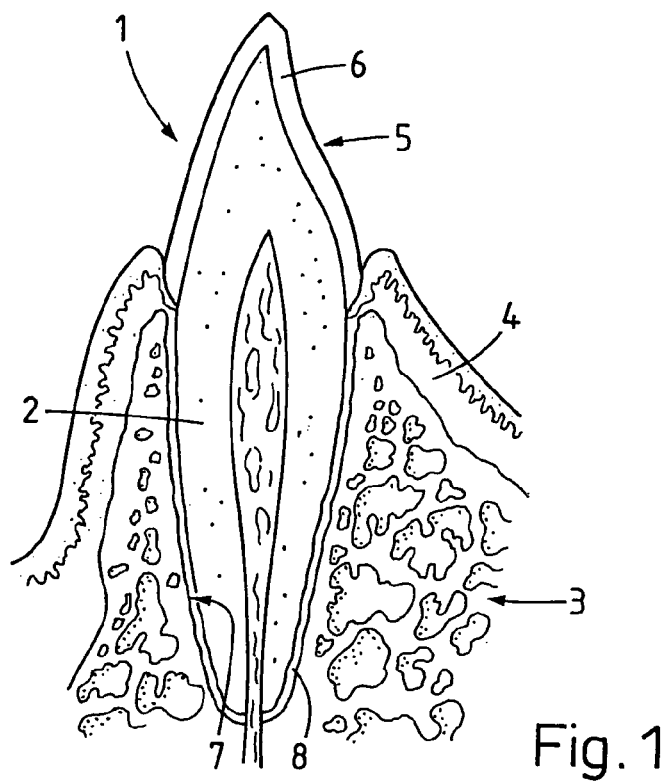
FIG. 1 shows a natural tooth in section across the jaw ridge.

FIG. 1 shows in section across the jaw ridge a natural tooth 1, whose root 2 is ingrown in a jawbone 3. The jawbone 3 is covered by gums 4 (connective tissue and skin). The crown 5 protrudes from the jawbone and gums 4 and is coated with a layer of dental enamel 6, while the interior of the crown 5 and the root 2 consist of dentine. The root 2 is located in an alveolus (tooth socket) in the jawbone, wherein the bone tissue of the alveolus wall 7 (alveolar bone), compared with bone tissue further removed from the root 2, usually has a greater density and therefore a superior mechanical stability. Between the alveolus wall 7 and the root 2 lies the tooth membrane 8 containing collagen fibres by which the root 2 is attached to the alveolus wall 7. The fibres carry the tooth and couple forces acting on the tooth laterally into the bone tissue. On extraction of the tooth, the tooth membrane is destroyed. It does not regenerate.

Figure 2:
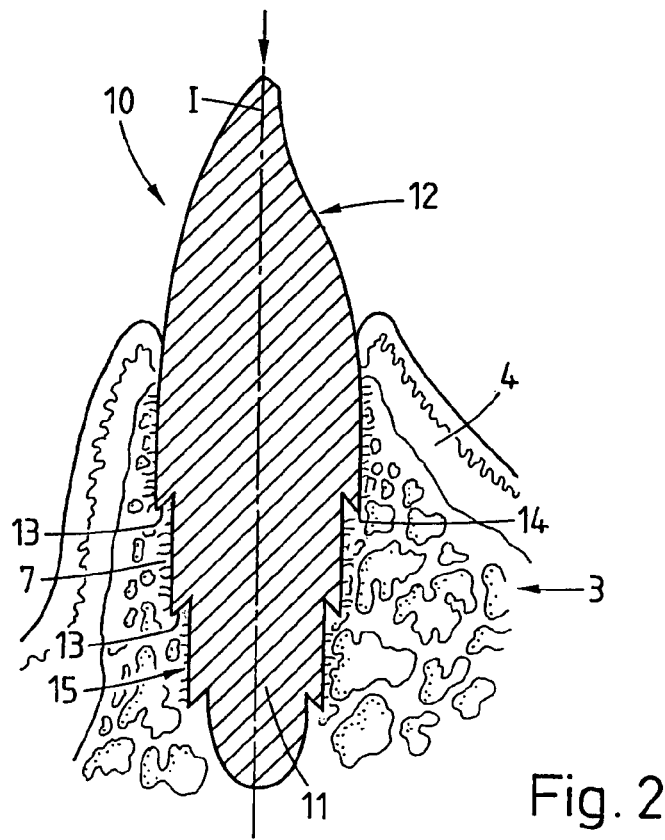
FIG. 2 shows an individual dental implant according to the invention replacing the tooth according to FIG. 1.

FIG. 2 shows, in section similar to FIG. 1, an individual dental implant 10 according to the invention, which replaces the tooth 1 illustrated in FIG. 1 by being implanted in the jawbone 3 in its place (implantation direction or implant axis I). The dental implant 10 comprises in the illustrated case not only a root portion 11 essentially adapted in its form to the root of the tooth 1 and the alveolus wall 7 but also a crown portion 12 adapted to the crown 5 of the natural tooth. The dental implant 10 is e.g. a single piece and consists of titanium, wherein the crown portion is coated in a ceramic layer (not shown) and the surface of the root portion 11 may be equipped, at least locally for an osseointegrative effect, or is at least biologically compatible and bone-friendly. Instead of the crown portion 12, the dental implant may comprise an abutment or a means for mounting an abutment, a crown, a bridge, or a set of dentures.

The root portion 11 of the dental implant 10 is tapering toward the distal end and comprises steps 13, whose outer edges are designed as cutting edges 14 facing towards the distal end region, and being lodged in the alveolus wall during implantation. Between the steps 13, the cross section of the implant remains essentially constant or is reduced continuously toward the distal end. In areas 15 between the steps, the implant is connected to the bone tissue of the alveolus wall 7 by the thermoplastic material. As already mentioned above, these connections are created during implantation. By means of mechanical vibration impinged on the implant, the thermoplastic material is liquefied and pressed into unevennesses and pores of the alveolus wall, where it remains anchored after re-setting, interlocking implant and bone by form fit and/or material fit.

Figure 3:
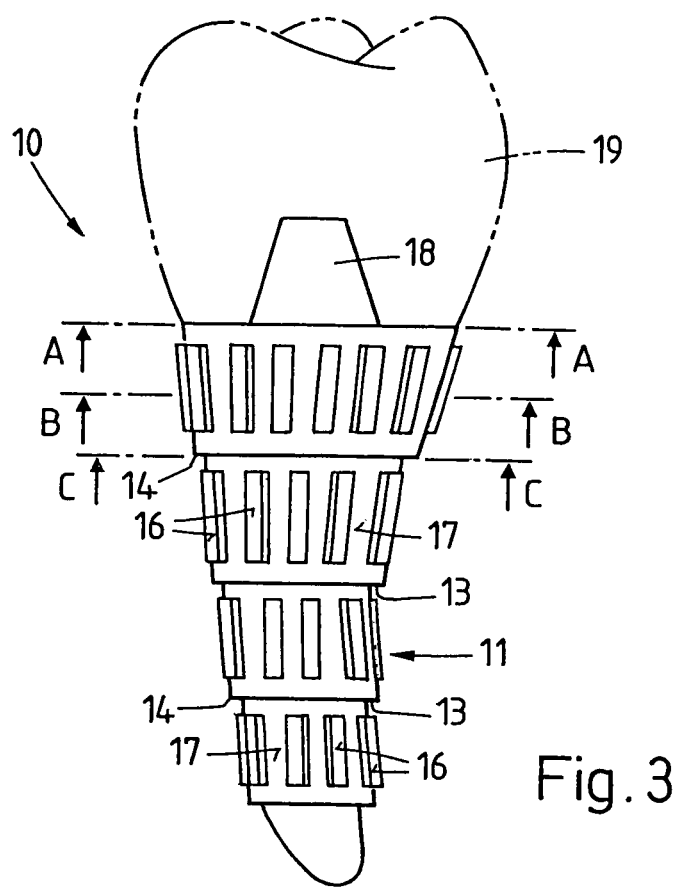
FIG. 3 is a lateral view of a preferred embodiment of the dental implant according to the invention.

FIG. 3 shows a similar individual dental implant 10 as does FIG. 2, but prior to implantation. On the root portion 11 of this implant the cutting edges 14 and the steps 13 are clearly visible, as are the surface ranges 16 of thermoplastic material situated between them and protruding from the surrounding surface areas 17. The surface areas 17 are biologically compatible, advantageously equipped for osseointegration. If the thermoplastic material is resorbable, the entire surface of the root portion 11 is advantageously equipped for osseointegration.

The shape of the root portion 11 is at least in part adapted to the shape of the natural root to be substituted, or to a mechanically relevant part of this root, and to the shape of the corresponding alveolus wall, i.e. it generally comprises the same cone shape with at least some of its cross sections not being round and/or its axis not being straight. Unlike the natural root and the alveolus wall however, the root portion 11 of the implant comprises steps 13, at least some of whose edges are designed as cutting edges 14, and surface ranges 16 of thermoplastic material protruding from the osseointegrative surface areas 17. The surface ranges 16 of the thermoplastic material are arranged and dimensioned in such a manner that as little as possible of the material which is liquefied during implantation is pressed on the osseointegrative surface areas 17, so that those can commence their osseointegrative effect immediately after implantation.

Figure 4:
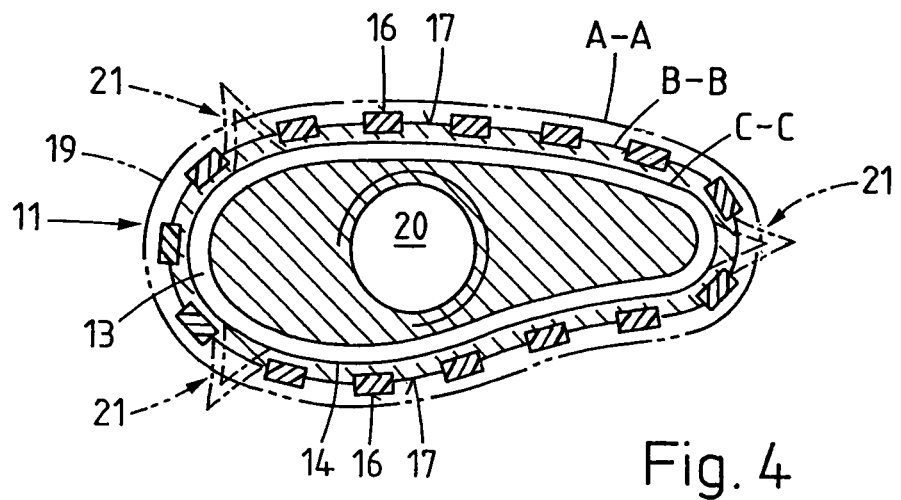
FIG. 4 shows three cross sections through an individual dental implant projected over each other (section lines A-A, B-B and C-C in FIG. 3)

FIG. 4 shows three cross sections (section lines A-A, B-B and C-C in FIG. 3) through the implant according to the invention, corresponding e.g. with the dental implant in FIG. 3. It is clearly evident from the cross section B-B that the surface ranges 16 of the thermoplastic material protrude from the surrounding surface areas 17.

As already mentioned earlier and as shown by chain line in FIG. 4, an implant according to the invention may additionally comprise furrowing or tapping edges 21 extending essentially axially and being dimensioned to cut into the cavity wall during implantation. Such structures lend the implant an additional component of primary stability, in particular with regard to torsional forces, and they continue to couple torsional forces acting on the implant into the bone tissue after osseointegration.

Good results can be achieved if the root portion 11 of a dental implant according to the invention is dimensioned as follows:

The cross sections of the root portion 11 are of similar size as the corresponding cross sections of the corresponding alveolus (root with tooth membrane). The cutting edges 14 and possibly the steps 13 and the axially extending furrowing structures 21, as well as the surface ranges 16 with the thermoplastic material protrude from these diameters.

The axial distances between neighbouring steps 13 on the one hand depend on the depth of the steps and the local steepness of the root portion. On the other hand it may be advantageous to increase the step depth particularly in proximal direction, and to reduce the distances, and possibly to fashion the cutting edges slightly salient so that they penetrate deeper into the alveolus wall in order to optimally anchor the implant.

The depth of the steps 13 does not exceed 1 mm and preferably lies between 0.1 to 0.5 mm. It is further limited by the space available between two teeth. If the steps protrude by more than ca. 0.3 mm beyond the dimension of the alveolus wall, it is advisable to fashion corresponding shoulders in the alveolus wall before implantation.

The surface ranges 16 of the thermoplastic material protrude by 0.05 to 2 mm (preferably 0.2 to 1 mm) beyond the surrounding surface areas 17.

The surface ranges 16 of thermoplastic material advantageously cover 10 to 50% of the total surface of the root portion 11 and extend advantageously in axial direction between the surface areas 17.

In line with the expected load collective, the above specifications can be adapted for other than dental implants. Providing that the corresponding bone mass is available, the depth of the steps can indeed be increased, in order to correspond not only with the steepness of the cavity but also to allow the forces to be optimally coupled so that the bone is sufficiently stimulated without excessive local stress. The loads coupled to the bone tissue through the cutting edges and the steps should, after osseointegration, induce stretching of the bone tissue of on average no more than 0.5% but no less than 0.05%.

The mentioned other implants are e.g. shafts of joint prostheses to be implanted in accordingly prepared tubular bones (e.g. hip joint, knee joint or finger joint prosthesis) and being adapted to an epiphyseal, metaphyseal and diaphyseal geometry, or to a cavity to be created or being existent in this geometry. The implants may also be implants for the repair of damaged bone areas (e.g. defects in the region of skull or jaw or caused by a tumorigenic disease in any bone area). It may also be considered to apply the invention on replicas of existing implants, wherein in a revisional operation with only minimal loss of vital bone tissue, an existing implant is replaced by an individual implant adapted to the existing implant or to the cavity resulting from the extraction of the existing implant.

The surface ranges 16 of thermoplastic material advantageously comprise energy directors, i.e. these surfaces comprise edges or points, or they comprise patterns of projections. The energy directors lead to concentrations of tension when the implant positioned in the bone tissue is excited by mechanical vibrations, and they ensure that the thermoplastic material begins to liquefy in regions in contact with the bone material and/or that the thermoplastic material can be liquefied at all.

The thermoplastic material is advantageously selected and placed upon the implant in such a manner that by application of the mechanical vibration the entire implant is acoustically excited, i.e. functions as a resonator. Thus the mechanical oscillations are not relevantly attenuated inside the implant, in particular at contact surfaces between non-thermoplastic material and thermoplastic material, or within the thermoplastic material. Consequently the thermoplastic material liquefies on the implant surface, in particular where the energy directors are in contact with the bone tissue. To ensure little damping within the thermoplastic material, advantageously a material with an elastic modulus of at least 0.5 GPa is selected. In order to prevent energy loss in the border areas between the two materials the connection of the thermoplastic material with the non-thermoplastic material is advantageously rigid and has a surface which is as large as possible.

When using ultrasonic energy for implantation, the thermoplastic material can be pressed into the bone tissue during implantation up to a depth of about two trabecular chambers, i.e. to a depth in the range of ca. 0.2 to 1 mm. To achieve such a penetration depth, the thermoplastic material must be present in an appropriate amount, and the implant design is to ensure a sufficiently large radial force between the surface areas of the thermoplastic material and the cavity wall.

As evident from FIGS. 2, 3 and 4, in addition to the root region 11 the dental implant may comprise e.g. a crown region 12 (FIG. 2), or a cone 18 for mounting an artificial crown 19 (FIG. 3), or a means (e.g. pocket hole 20 with internal thread, FIG. 4) for affixing a cone, an abutment, or a fastening implement for a bridge or for a set of dentures. Such constructions are well known from the state-of-the-art technology.

Figure 5A:
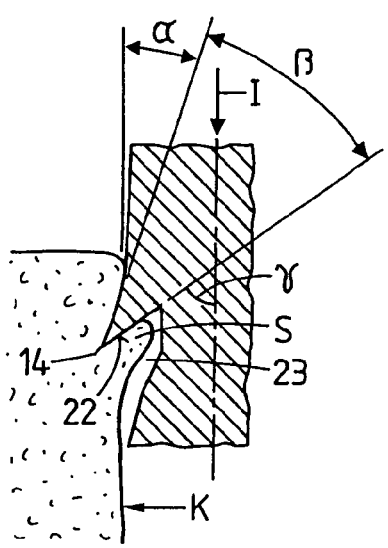
FIGS. 5A and 5B are axial sections through the area of a cutting edge of an implant according to the invention.
Figure 5B:
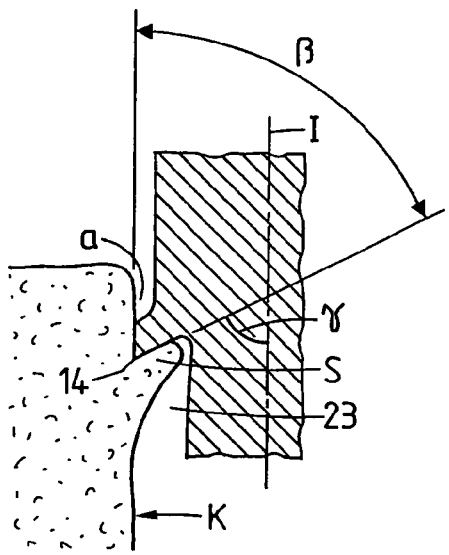

FIGS. 5A and 5B each show an axial section of a cutting edge 14 of an implant according to the invention at a slightly larger scale, wherein the implant is shown with the proximal end facing upwards and the distal end downwards. The cutting edge 14 faces toward the distal implant end (which is downward in FIGS. 5A and 5B) and comprises a wedge angle $\beta$ of less than 90° (advantageously 45° to 80°). It is designed slightly salient from the implant axis. Depending on the design of such projection this results in a clearance angle α (FIG. 5A) or a clearance space a (FIG. 5B) in relation to a cavity wall K (bore) extending parallel to the implant axis I. Such clearance reduces friction between the cavity wall and the implant and therewith reduces heat production. The clearance angle α is advantageously small (e.g. 1° to 15°) and the depth of the clearance space is e.g. 0.1 to 0.3 mm. To enable the cutting edge 14 to cut and form a chip, the cutting angle amounting to α+13 is less than 90°, or the angle γ between the chip supporting surface 22 and the implant axis I is less than 90°. The chip S being formed from the cavity wall by the cutting edge is pushed into an undercut under the chip supporting surface 22 which serves as chip space 23. Depending on the size of this chip space 23 the effect of the cutting edge 14 is not only a cutting effect but also a compressing effect in which the bone tissue is densified.

If the implant with a cutting edge 14 similar to the ones shown in FIGS. 5A and 5B is implanted in a slightly conic cavity (cavity wall K not parallel to implant axis), the cutting edge does not need to be salient; the clearance angle α then being e.g. equal to the angle between the cavity wall K and the implant axis I.

FIG. 6 shows, again in axial section, a series of cutting edges 14, 14' and 14" being arranged behind each other in the direction of implantation (in FIG. 6 downwards) and designed in a similar way as the cutting edge shown in FIG. 5A. The distance between the cutting edges and the implant axis I decreases in implant direction, thus enabling the cutting edges to work consecutively when forming chips on a cavity wall K (K' before the impact of the cutting edges) which extends parallel to the implant axis I. Obviously, in such a case too, the cutting edges 14, 14' and 14" are combined with reductions in cross section which are as small as possible. Unlike with a conic implant (e.g. according to FIGS. 2 and 3) however, the depths (d) of the steps are not dependent on the general shape of cavity or implant but can be designed for optimal cutting and chip forming and therewith anchoring of the implant. For a dental implant to be implanted in a corresponding bore the depths or the steps advantageously do not exceed 0.3 mm.

If the chip spaces 23 are not large enough for the total chip material on the implant side of the cutting edge (chip), the latter is compressed therein. To avoid excessive compression at least part of this material may be removed e.g. through channels 25, e.g. by sucking off or rinsing. If the material is removed by rinsing, care is to be taken that the implant design permits the material removed by rinsing (chip material and rinsing agent) is able to drain from the cavity between cavity wall and implant.

Figure 7:
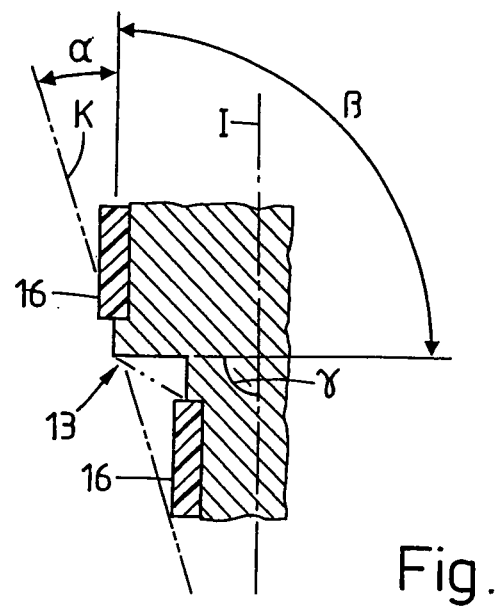
FIG. 7 is an axial section through a step-shaped reduction in cross section (step) of an implant according to the invention, the step not being equipped with a cutting edge.
Figure 8:
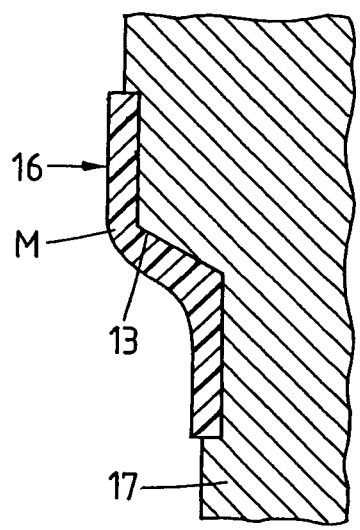
FIG. 8 is an axial section through a step with liquefiable material extending across it.

FIG. 7 shows, again in axial section, a step 13 (step-shaped reduction in cross section), which is not equipped with a cutting edge (cutting angle α+β=90° in a bore, in which the cavity wall is parallel to the implant axis I, or greater than 90° in a conic cavity with the cavity wall K; angle γ equal or greater than 90°), and therefore at best acts in a scraping manner on the cavity wall. On conic implants such steps 13 can be provided in addition to steps with cutting edges. Also visible in FIG. 7 are the surface ranges 16 of the liquefiable material M, wherein the liquefiable material is situated in depressions and protrudes from the surrounding surface areas. If a step 13 is not equipped with a cutting edge, the liquefiable material and the depression associated with it may extend across the step, as shown in FIG. 8 in another axial section through such a step 13.

Figure 9:
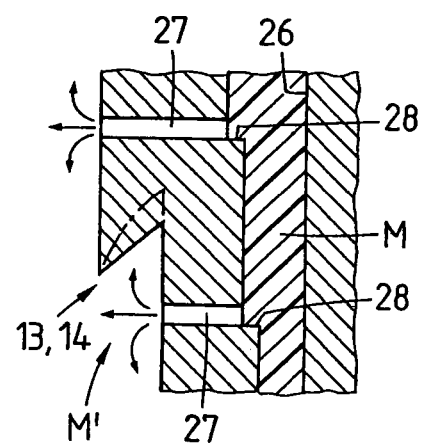
FIG. 9 is an axial partial section through an embodiment of the implant according to the invention, with a liquefiable material positioned in a hollow space of the implant.

FIG. 9 shows, again in axial section, an implant according to the invention, which comprises a hollow space 26, in which the liquefiable material M is positioned before the implantation, and openings 27 through which the liquefiable material is pressed to the implant surface, when liquefied (M') during implantation. The pressed out material forms then surface ranges on the outer side of the implant and, after re-solidification, an anchoring between bone tissue and implant. The hollow space 26 is advantageously provided with energy directors 28, e.g. in the shape of angular shoulders, to minimise the energy consumption for an optimal liquefaction of the liquefiable material and low viscosity thereof.

Figure 10:
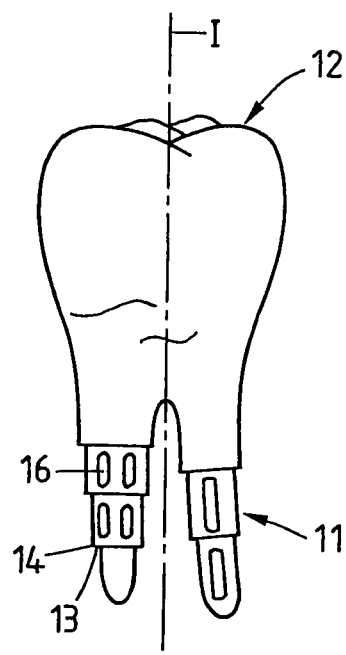
FIGS. 10 to 12 show three exemplary dental implants according to the invention.

FIG. 10 shows, as a further example of an implant according to the invention, an individual dental implant comprising a multiple root portion 11 like a natural molar. This root portion 11 does not necessarily need to substitute the entire natural root but may be limited to its mechanically relevant and/or extractable parts. In this case too, it is possible to implant the implant immediately after the extraction of the molar and to load it immediately after implantation. The implant may thus comprise a crown portion 12 which is e.g. a replica of the crown of the extracted tooth.

Figure 11:
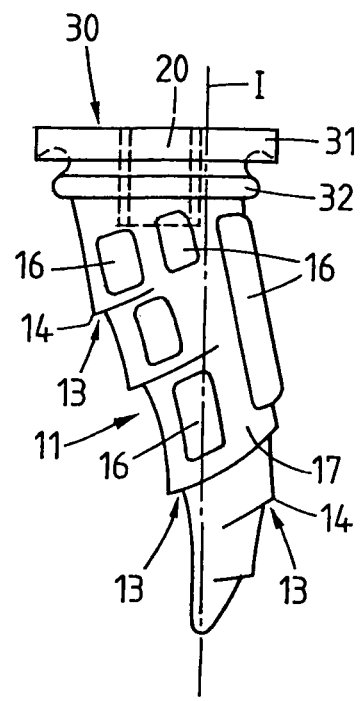

FIG. 11 shows a further individual dental implant according to the invention, again comprising a root portion 11 with steps 13, which are at least in parts equipped with cutting edges. These steps 13 are axially irregularly distributed on the root portion 11 and do not fully extend around it and rather oblique than perpendicular to the implant axis I. Accordingly, the surface ranges 16 of thermoplastic material and the osseointegrative surface areas 17 form an irregular pattern. The implant further comprises an abutment-like proximal part 30 which, after implantation, protrudes from the jawbone into the gums and which, for the fastening of further parts, is equipped e.g. with a pocket hole 20 having an internal thread. The abutment 30 comprises a collar 31 whose lower edge is undercut to form a cutting edge. After implantation, the abutment 30 is supported by this lower edge which cuts slightly into the surface of the jawbone. Below the collar 31 there is a ring 32 of thermoplastic material, which is to anchor the implant in the outer layer of the jawbone by liquefying during implantation. In particular for older patients, this ring 32 consists advantageously of a non-resorbable thermoplast, so that it can assume, in addition to its anchoring function, a function of insulating the bone tissue such enhancing the insulation function of the gums, which may be unable to fit tightly around the implant.

Collar 31 and ring 32 may be designed to be functionally independent of each other. Furthermore, they can be used individually or in combination on standardized dental implants as well as on other, non-dental implants for anchoring the implant in a bone surface and for tightly closing the bone cavity around the implant.

The shape of the implant according to the invention not being that of a circular cylinder or a circular cone, and in the case of an individual implant not being rotationally symmetrical at all, the orientation of the implant in the cavity is defined precisely. For this reason it is possible to design the collar 31 not in a plane perpendicular to the implant axis, and not round (rotationally invariable), as shown in FIG. 11, but adapted to the natural tooth, i.e. about oval and curving like the natural jaw ridge (scalloped).

Figure 12:
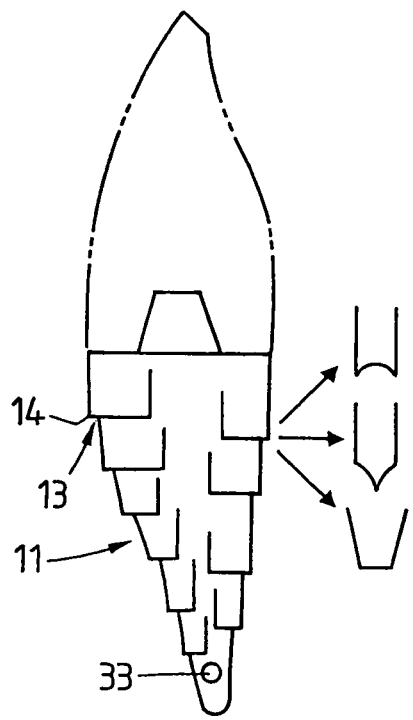

FIG. 12 shows a further implant according to the invention, which again as an example is designed to be a dental implant. The implant therefore comprises a root portion 11 with steps 13 equipped at least partially as cutting edges 14 and in this case limited to parts of the implant circumference, so that they project like scales from the rest of the implant surface. These scaly structures may be essentially rectangular or square, as illustrated on the root portion 11, with edges extending along the circumference (lower edges), which may be blunt or cutting, as described above (FIG. 5 to 7). The same applies to the essentially axial edges of the scaly structures which, if designed to cut, function as axially extending furrowing or tapping structures.

On the right of the root portion 11, FIG. 12 shows further exemplary shapes of steps 13 having scaly shapes. These may comprise e.g. in axial direction concave (curving toward central or lateral points) or convex (not shown) lower edges, or axial edges leaning at an angle toward the lower edge. In radial direction too, these lower edges and areas above the lower edges can be even or convexly or concavely curved, the "scale" thus being shaped straight or in the form of a cone or hollow cone.

It is also possible to provide the root portion 11 of the individual dental implant in a per se known manner with a through opening 33 or a plurality thereof. During the osseointegration phase bone tissue grows through such openings.

Figure 6:
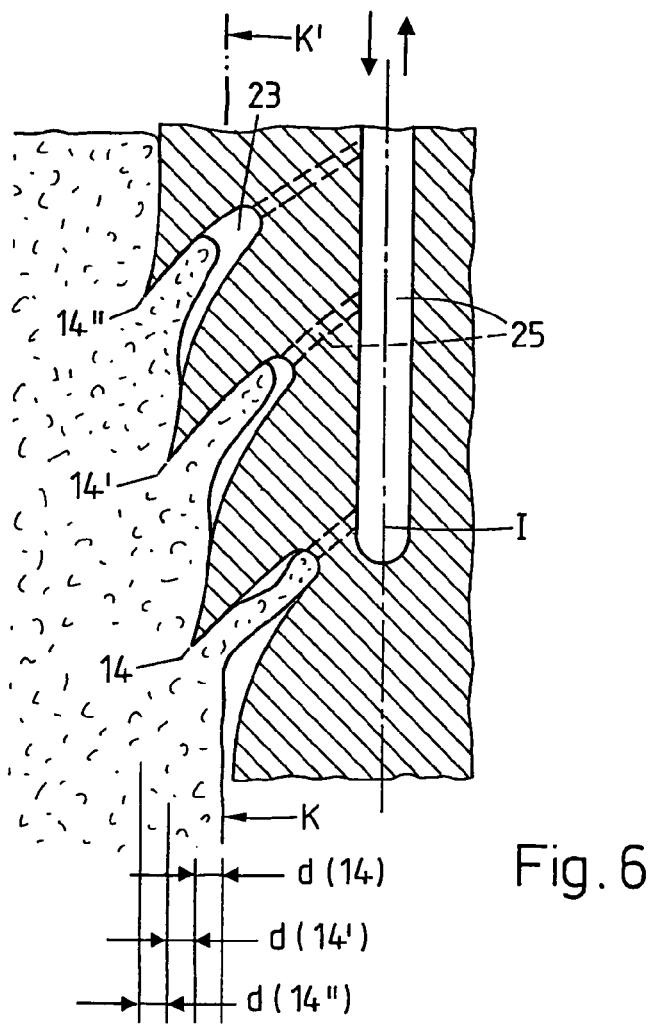
FIG. 6 is an axial section through a series of cutting edges of an implant according to the invention, the cutting edges being arranged consecutively in implanting direction.
Figure 13:
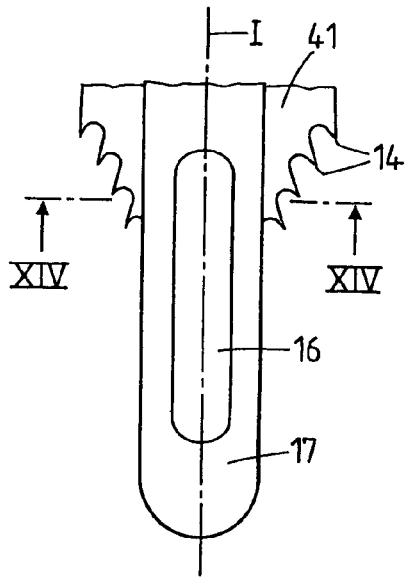
FIGS. 13 and 14 show an implant according to the invention, which is suitable for implantation in a bore, viewed from the side (FIG. 13) and sectioned at right angles to the implant axis (FIG. 14, section line XIV-XIV in FIG. 13)
Figure 14:
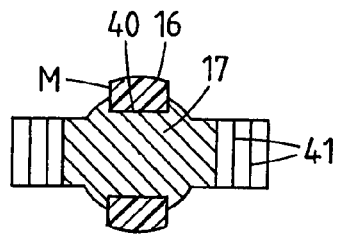

FIGS. 13 and 14 show a further embodiment of an implant according to the invention which may be used e.g. as dental implant. FIG. 13 presents the implant viewed from the side, FIG. 14 as a section at right angles to the implant axis I (section line XIV-XIV in FIG. 13). The implant is essentially cylindrical and designed to be implanted in a cylindrical bore. On two sides facing each other in relation to the implant axis, the implant comprises surface ranges 16 of thermoplastic material M, wherein the thermoplastic material is situated in depressions 40 (here grooves closed in axial direction) and protrudes from the surrounding surface areas 17. On the implant circumference between the surface ranges 16 with the thermoplastic material and facing the proximal implant end, there are protruding regions 41 bearing the cutting edges 14. These extend essentially transverse to the implant axis and are distanced from the implant axis, the distances decreasing in implanting direction, as illustrated in FIG. 6. From cutting edge to cutting edge these distances differ by about 0.3 mm (for dental implant) so that the implant can be implanted in a cylindrical cavity (bore) without prior form adaptation. In other words, the cutting edges 14 are designed in such a manner that each cutting edge changes the cavity wall by cutting a chip from the cavity wall, thus allowing the following cutting edge to again cut a chip. The distances between the axially aligned cutting edges, measured at right angles to the implant axis, may exceed 0.3 mm for implants larger than dental implants.

The implant according to FIGS. 13 and 14 is thus implanted in a rotationally invariant cavity (circular cylindrical bore) and yet is stabilized against tortional loading after implantation by its non-rotatable shape. Compared to a screw-shaped implant the one presented here has the advantage that it can be implanted in an exactly predetermined rotational position and therefore can also bear abutments other than rotationally invariant ones, e.g. a scallopped collar, a crown, etc.

For the implant according to FIGS. 13 and 14 it is not a condition that the depressions 40 provided for the thermoplastic material are axially extending grooves. These grooves may in particular extend spirally such improving the capability of the implanted implant to absorb torsional forces. If the implant according to FIGS. 13 and 14 is to be implanted in a stepped bore or in a cavity with a cone-like narrowing inner end, it may, in addition to the cutting edges, comprise steps (not shown). Therein depressions 40 and the liquefiable material placed in the depressions may continue across the steps as illustrated in FIG. 8.

Figure 15:
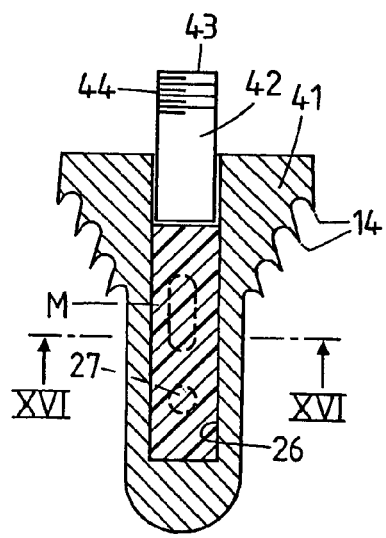
FIGS. 15, 16A and 16B show a further implant according to the invention which is suitable for implantation in a bore and in which the liquefiable material is positioned in a hollow space; sectioned axially (FIG. 15), sectioned at right angles to the implant axis (FIG. 16A, cutting line XVI-XVI in FIG. 15) and viewed from the side (FIG. 16B)
Figure 16A:
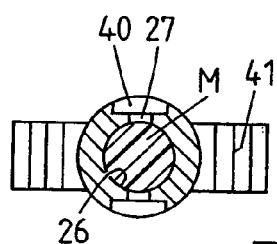
Figure 16B:
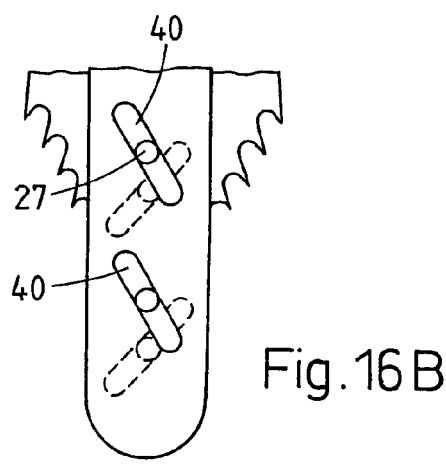

FIGS. 15, 16A and 16B show another implant according to the invention (FIG. 15: axial section; FIG. 16A: section transverse to the implant axis with section line XVI-XVI; FIG. 16B: side view), which is e.g. a dental implant in essence corresponding with the implant according to FIG. 13, but which comprises a hollow space 26 and openings 27 being e.g. essentially round or slit-shaped and connecting the hollow space 26 with the outer surface of the implant. The openings 27 open into the depressions 40, which comprise e.g. a roughened bottom surface for improving adhesion of the liquefiable material. The liquefiable material M, which in this case may be a thermoplastic or thixotropic material, is positioned in the hollow space 26 prior to or during implantation and is at least partly liquefied with the aid of mechanical vibration and pressed through the openings 27 into the depressions 40. These depressions form pockets between implant and cavity wall into which the liquefied material is pressed and thus brought into intensive contact with the cavity wall. As evident from FIG. 16A, the depressions 40 can be designed as grooves gyrating around the implant. This is particularly advantageous for an implant with a hollow space 26, because the gyrating grooves do not tend to turn the implant on implantation but still, after implantation stabilize the implant better against rotation in the cavity.

The implant according to FIGS. 15, 16A and 16B is advantageously implanted without liquefying the liquefiable material M, i.e. is brought into its final position in the cavity, for which purpose it is driven home with a customary tool or pressed in with a mechanically oscillating element (e.g. sonotrode of an ultrasonic device). The implant position is then checked and if necessary slightly adjusted with regard to depth and rotational position. Only then the liquefiable material is impinged with mechanical oscillations and pressed against the distal end of the implant, whereby it is liquefied and emerges through the openings 27, filling the depressions 40 and penetrating the surrounding bone tissue. To grant the implant sufficient stability in the cavity during said check and possible adjustment of its position, it may be advantageous to slightly oversize the dimensions of the implant with regard to the cavity in such a manner that not only the cutting edges lodge into the bone tissue but the implant is held in the cavity by a press-fit.

To liquefy the liquefiable material, a sonotrode adjusted to the cross section of the hollow space 26 may be used or a piston 42, which is a component of the implant. For coupling the mechanical oscillations into the piston, a sonotrode is positioned on the proximal end 43 of the piston 42. The piston 42 is designed to penetrate into the hollow space 26 with increasing liquefaction and displacement of the liquefiable material until its proximal end 43 reaches into the opening of the hollow space 26. The piston 43 consists e.g. of titanium and is equipped with a fine-pitch thread 44 in the region of its proximal end 43, which fine-pitch thread, when pushed into the hollow space 26 is cold-welded to the wall of the hollow space, if this consists of titanium also. Thus the proximal opening of the hollow space 26 is sealed tightly, guaranteeing insulation between the oral cavity and the bone tissue, which insulation is vital for a dental implant. If the liquefiable material is resorbable, the bone tissue will gradually replace it after implantation, i.e. it will grow into openings 27 and hollow space 26, wherein it is all the more important that the hollow space 26 is tightly sealed from the oral cavity.

Figure 17:
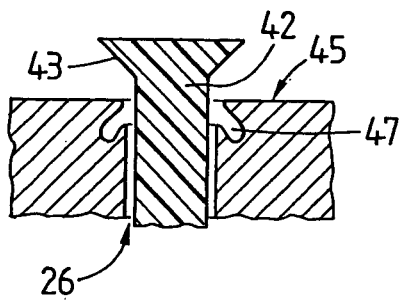
FIGS. 17 and 18 show details of implants according to FIGS. 15 and 16.

FIG. 17 shows in an axial section like FIG. 15, a piston 42, positioned in the proximal opening of the hollow space 26 in order to displace the liquefiable material. The piston is designed in such a manner that its proximal end 43 reaches the proximal surface 45 of the implant when sufficient liquefiable material has been pressed out of the hollow space 26 through the corresponding openings 27 on to the outer surface of the implant. The proximal piston end 43 is broadened cone-like and the piston 42 consists in this case of thermoplastic material, e.g. of PEEK. When the edge around the proximal opening of the hollow space 26 comes in contact with the oscillating broadened end of the piston 43, it acts as energy director and causes tension concentrations by which the thermoplastic material is liquefied. The liquefied material penetrates between the wall of the hollow space 26 and the piston 42, where a lining groove 47 is advantageously provided, and thus, together with the piston 42, closes the proximal opening of the hollow space 26 tightly.

FIG. 18 again shows an axial section through an implant according to the invention, which comprise a hollow space 26 connected to the outer implant surface by openings 27. In order that the liquefiable material, in this case a thermoplastic, is liquefied by the effect of the mechanical oscillations specifically in the region of the openings 27, energy directors 28, e.g. in the shape of sharp edges extending along the periphery of the hollow space 26, are provided at the inner outlets of the openings 27. At the distal end of the hollow space 26 e.g. a thorn-shaped energy director 28 may be provided. A piece of the liquefiable material, which is advanced in the hollow space 26 and is impinged with mechanical oscillations, strikes the energy directors 28, which results in local stress concentrations in the oscillating material and local liquefaction thereof.

Figure 18:
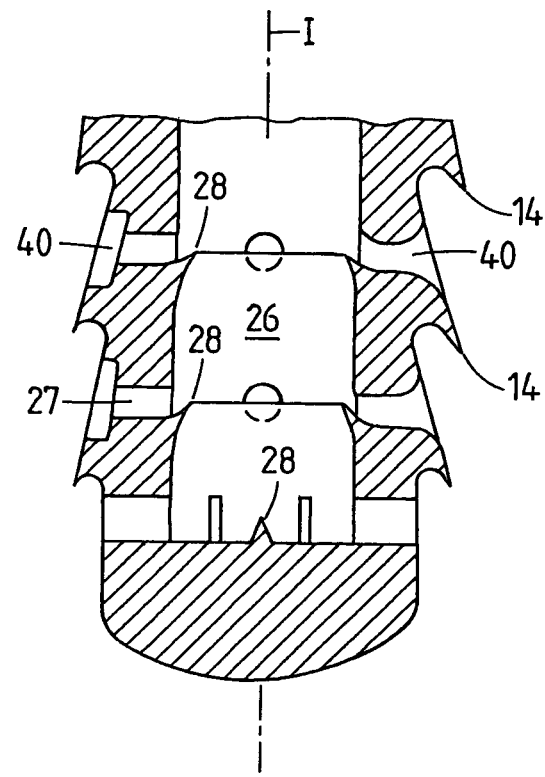

Also evident in FIG. 18 are the various embodiments of openings 27 and their outlets into depressions 40. The cross section of the openings 27 is e.g. round (top, in FIG. 18) or slit-shaped (bottom, in FIG. 18) and the depressions can be separated from the openings by an edge (left of FIG. 18) or can be designed as widening outlets of the openings (right of FIG. 18). Combinations of the listed characteristics may also be considered.

Figure 19:
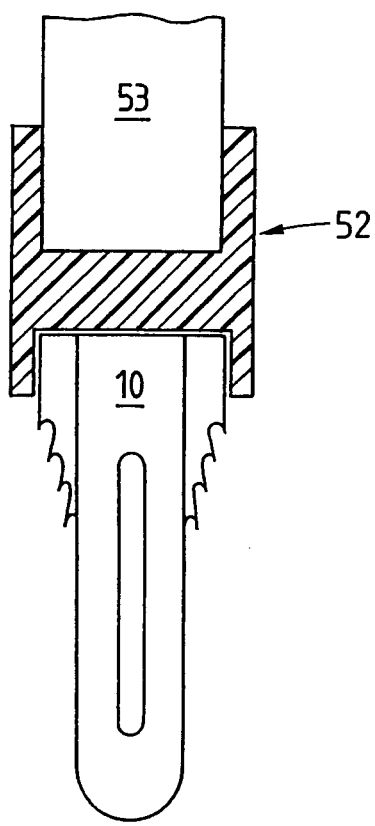
FIG. 19 shows an implant according to FIGS. 13 and 14 with an intermediate element.

FIG. 19 shows on the basis of the exemplary implant according to FIGS. 13 and 14 a intermediate element 52, which is suitable for implanting the implant by means of mechanical oscillation, in particular ultrasonic oscillation. On the implant side, the intermediate element 52 is adapted to the proximal end region of a specific, possibly individual implant 10, and on the excitation side it is adapted to an advantageously standardized sonotrode 53, which is part of an ultrasonic device. The connection of the intermediate element is on either or on both sides advantageously designed as a loose fit, i.e. as a connection with play in axial direction and guiding function in radial direction. The other connection may be fixed, e.g. a frictionally engaged clamp fit or screwed connection.

The intermediate element 52 advantageously consists of a material (e.g. PEEK) with little acoustic attenuation (high elastic modulus) and may be designed in a corresponding manner or made of a corresponding material in order to be able to acoustically adapt the implant 10 and the sonotrode 53. This means that in addition to its interface function between the standardized sonotrode geometry and a specific implant geometry, the intermediate element 52 can have a function of acoustic adaptation; it may furthermore carry markers for orientation and measuring purposes during implantation; it may serve as a part which does not directly belong to the implant and is easily accessible to the surgeon, rendering the implant, particularly in the case of a relatively small dental implant, easier to handle. Advantageously the intermediate element 52 is mounted on the implant 10 during production and is disposed of after implantation. Such it can also present a part of the implant packaging. If the intermediate element 52 consists of a transparent material, it can also adopt a light transmitting function, wherein light for illuminating the cavity and the implant is coupled into the element from the sonotrode side.

A loose fit connection between implant 10 and intermediate element 52, and/or between intermediate element 52 and sonotrode 53 (or between sonotrode and implant if no intermediate element is used), can only transmit axial oscillation components directed towards the implant, i.e. those driving the implant into the cavity. Oscillation components drawing the implant from the cavity are not transmitted. Experience shows that the implantation by means of half-waves created with the named loose fit connection is advantageous. One reason for this is probably the fact that there is no pulling-out motions of the implant in the cavity and therefore less frictional heat is created between cavity wall and implant. A further advantage of the loose fit connection is the fact that it separates the implant acoustically from the sonotrode, and from the intermediate element if applicable, and that therefore exact acoustic tuning between exciting parts and implant becomes less important.

The loose fit connection is realized e.g. by a gap between implant and intermediate element, which acts like a capillary and which is supplied with liquid immediately before implantation. The implant being inserted in the intermediate element and facing upwards is mounted on the sonotrode, and then liquid, e.g. water, is applied between the proximal end of the implant and the intermediate element. Due to the capillary effect the liquid spreads between the two parts and holds them together sufficiently for the implant to be turned to face downwards without dropping out of the fit.

Figure 20:
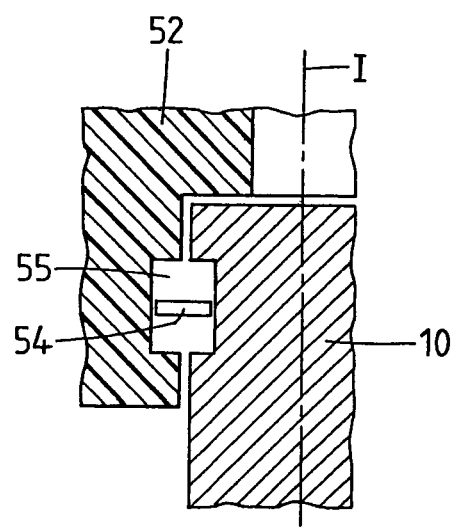
FIG. 20 shows an exemplary embodiment for a loose fit connection between implant and intermediate element, or between intermediate element and sonotrode (axial section)

FIG. 20 shows in an axial part section a further embodiment of a loose fit connection between an implant according to the invention 10 and an intermediate element 52 (or between the intermediate element and the sonotrode, or between the implant and the sonotrode). This loose fit connection essentially comprises a tension ring 54, positioned in aligned axially oversized snap ring grooves 55, one on the implant 10 and the other one on the intermediate element 52, and consisting of a material that can hold the weight of the implant yet allows destruction of the ring for separating the implant from the fit with little force. Further embodiments of loose fit connections are known by one skilled in the art and may be similarly applied to the case on hand.

As shown in FIG. 20, the intermediate element 52 need not fill the whole space between sonotrode 53 and implant 10. It may comprise openings or other suitable partly hollow structures.

Figure 21:
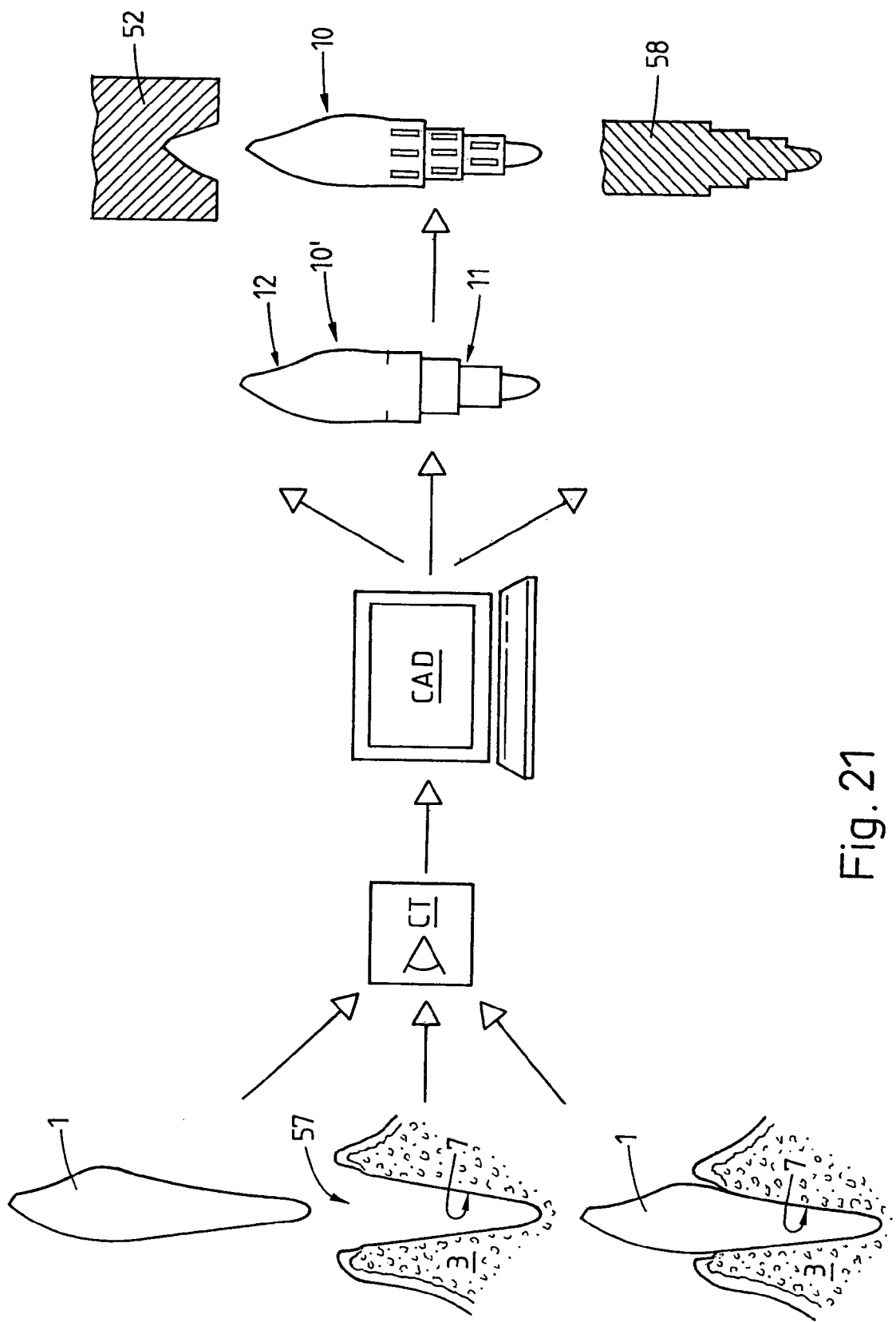
FIG. 21 is a diagram for illustrating the production of an individual dental implant according to the invention.

FIG. 21 illustrates the method of producing a dental implant 10 according to the invention. This method essentially comprises three steps, all of which are based on per se known methods. These steps are:

Taking measurements: A tooth 1 to be substituted and/or the corresponding alveolus 57, or alveolus wall 7 respectively, are measured in order to create e.g. a three-dimensional image. The measuring data representing the image are prepared for further processing.

Data processing: The measuring data representing the image are adjusted in particular by addition of cutting edges and structures of liquefiable material, and if applicable by adding oversize, or furrowing or tapping, axially extending structures. If the image is not a complete three-dimensional image, it is completed using shapes of implants based on experience. The processed measuring data are prepared for producing the implant.

Producing the implant: the implant is produced on the basis of the processed measuring data, if necessary in a series of production steps.

Various methods are suitable for the measuring step, in particular the method of computer tomography (CT) or an MRI-method (Magnetic Resonance Imaging), by which methods e.g. for a tooth, which is not yet extracted, an image of the tooth 1 and of the alveolus 57 can be created simultaneously. Such a method permits production of the implant prior to extraction of the natural tooth to be substituted, such that extraction of the tooth to be substituted and implantation of the implant in its place becomes possible in just one session.

It is nevertheless possible to measure the extracted tooth and/or the alveolus 57 after extraction, wherein particularly deformities of the alveolus caused by the extraction can be included in the measurements.

Instead of taking a three-dimensional image requiring complex appliances, it is also possible to take appropriate measurements from a two-dimensional X-ray image or from a plurality of such images. In order to create a three-dimensional model for the implant, the images are complemented by corresponding values based on experience.

The step of data processing is advantageously performed on a CAD-system (computer aided design), which is supplied with the data from the measuring step. If the measuring data of the alveolus 57 are available, the root portion of the implant is advantageously modelled on these data. If only the measuring data of the tooth to be substituted are available, a thickness of the tooth membrane based on experience may need to be added. An implant with a hollow space may need to be oversized for a press-fit. In addition, the lateral surfaces of the root portion are modified by adding the cutting edges and the surface areas of the thermoplastic material, and possibly the structures promoting osseointegration. Depressions on a preliminary implant 10' may need to be provided for the surface areas of the thermoplastic material, in which depressions parts of the thermoplastic material are provided, advantageously to be fixed by form-fit. For the osseointegrative surface areas e.g. appropriate surface structures are provided.

In the step of data processing, data may also be generated to provide a basis for the production of an intermediate element 52 which is adapted as accurately as possible to a proximal end of the implant, e.g. to its crown portion 12. Similar data can be generated for the production of a processing tool 58, or a set of such tools, wherein these tools are adapted to the root portion of the implant (slightly undersized for one processing tool, or gradually more undersized for a set of processing tools). The processing tool 58 serves for the preparation of the alveolus wall prior to implantation of the implant.

The step of producing the implant is advantageously performed by a CAM-System (computer aided machining), which is supplied with the data from the data processing step. In this step a preliminary implant is produced e.g. from an appropriate titanium blank e.g. by milling, grinding, or electro erosion. From this the osseointegrative surface areas are created by appropriate surface treatment and parts of thermoplastic material are mounted (by latching, gluing, molding, ultrasound, etc.), resulting in the completed implant 10.

The intermediate element 52 and the processing tool or tools 57 for the preparation of the alveolus wall are produced in essentially the same way as the preliminary implant 10'.

Figure 22:
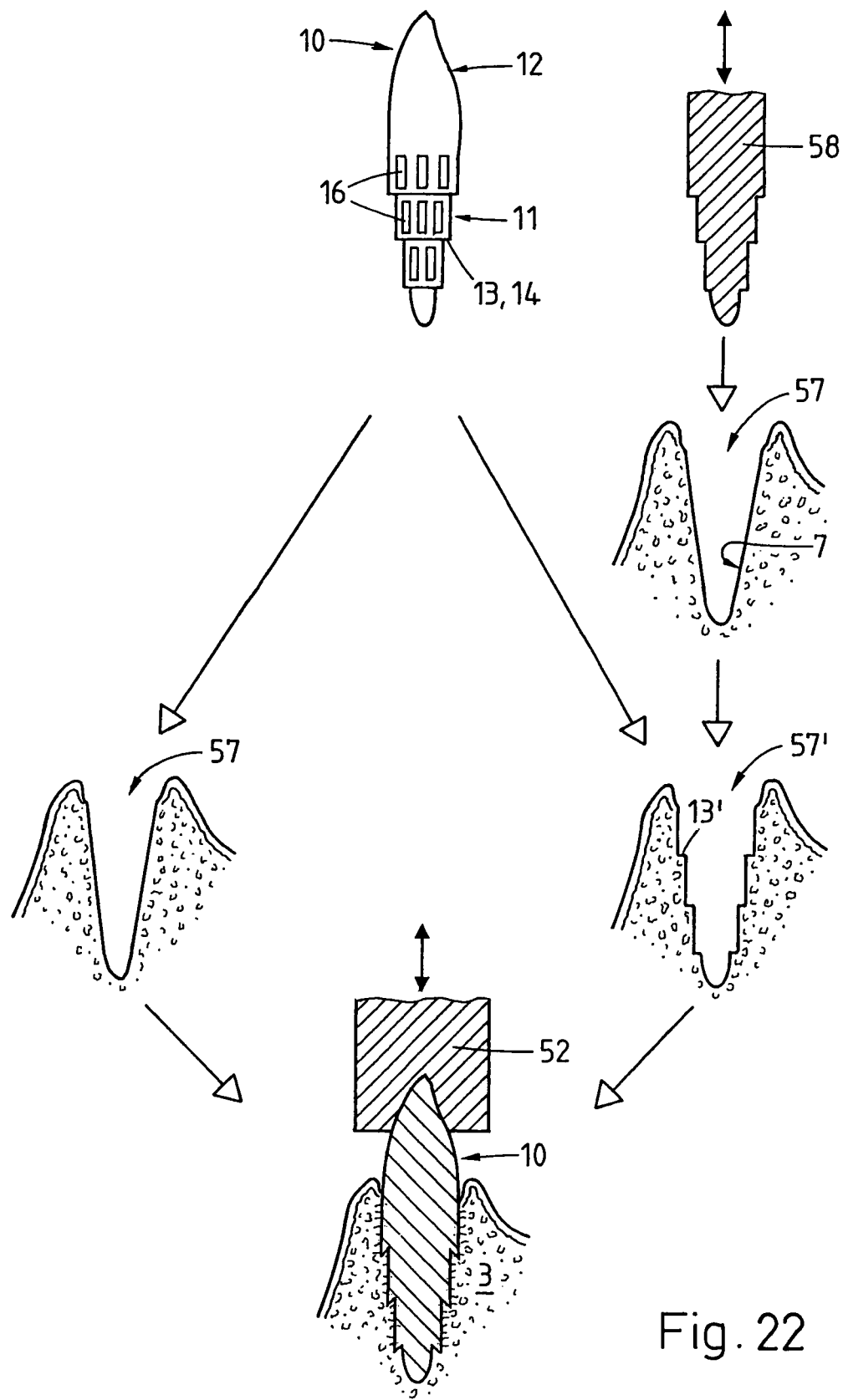
FIG. 22 is a diagram for illustrating the implantation of a dental implant according to the invention.

FIG. 22 illustrates the method for implanting a dental implant according to the invention, wherein the illustrated implant 10 comprises in addition to a root portion 11 equipped according to the invention also a crown portion 12, wherein both portions are adapted to the shape of a natural tooth to be substituted. The root portion 11 of the illustrated implant 10 comprises steps 13 with cutting edges 14 and surface ranges 16 of a thermoplastic material and if appropriate, axially extending furrowing or tapping geometries (not illustrated).

The alveolus 57 is cleaned and curetted prior to implantation with the aid of e.g. a tool driven by ultrasound (not illustrated). If the stress on the bone tissue caused by a direct implantation is tolerable, the implant is directly implanted in the alveolus 57 thus prepared (embodiment illustrated on the left of FIG. 22). If the stress on the bone tissue is to be kept low, the alveolus 57 is prepared with the processing tool 58 creating shoulders 13' in the alveolus wall 7 which correspond to the steps 13 of the implant (embodiment with processed alveolus 57' illustrated on the right of FIG. 22). For this preparation a processing tool 58 adapted to the root portion is introduced into the alveolus. The cross sections of the processing tool 58 should therein be slightly smaller than the corresponding measurements of the implant. If necessary, several such processing tools may be used, wherein each tool is slightly thicker compared to the previously used tool.

The alveolus is also prepared with corresponding tools if the implant is not individually adapted to the alveolus but a suitable, though standardized implant is to be used.

The processing tools 58 are placed in the alveolus by appropriate tapping. Advantageously however, they are excited by mechanical oscillations, preferably ultrasound, and are simultaneously guided into the alveolus. If necessary the processing tool 58 may be flushed with a slightly abrasive medium, which medium is pressed through an opening on the distal end of the tool to between tool and alveolus wall, and which medium also serves to carry off fragmented bone material.

The implant 10 is placed in the cleaned or appropriately processed alveolus (57 or 57'). The implant is impinged with mechanical oscillations, in particular ultrasound, advantageously during such placement of the implant into the alveolus. Of course it is also possible to place the implant in the alveolus by use of a hammering tool first and then to impinge it with ultrasound.

In particular if the implant comprises a crown portion 12, it is advantageous to use an intermediate element 52 which is adapted to this crown portion. If the implant comprises only a root portion with an essentially flat proximal surface or a standard construction, it is possible to also use an intermediate element 52, but it is possible also to use solely an appropriate standard sonotrode. By adapting the length and geometry of the sonotrode, and if applicable the intermediate element, the acoustic excitation of the implant can be optimized. For improved handling, the sonotrode or the intermediate element 52 may be equipped by suitable measures, such as form fit or material fit or by applying vacuum, to support the link to the implant (see also FIGS. 19 and 20 and corresponding parts of the description).

If the root portion of the implant only represents the mechanically relevant parts or the corresponding natural root but the natural root has been wholly extracted, the parts of the alveolus not to be occupied by the implant are advantageously filled with a bone replacement material before implantation, e.g. with calcium phosphate granules as used for augmentations.

Advantageously the implant is implanted as quickly as possible, i.e. immediately after the extraction of the tooth to be substituted.

Of course, it is also possible to create a cavity and prepare it for an implantation of the implant according to the invention as described above, in a place of the jawbone where there is no alveolus or where a former alveolus is filled with regenerated bone tissue. The shape of such a cavity and the corresponding implant can be adjusted to the bone structure, which can be measured like an alveolus e.g. by computer tomography.

FIGS. 23A to 23C illustrate implantation of a joint prosthesis whose shaft is equipped according to the invention. FIG. 23A shows a cross section through the bone 60 with the epiphyseal area 60.1, the metaphyseal area 60.2 and the diaphyseal area 60.3, in which the shaft of the joint prosthesis is to be implanted, wherein this shaft may be an individual implant specially produced for implantation in the specific bone or a suitable standardized implant. FIG. 23B shows the processing instrument 58 (also in cross section), whose shape essentially coincides with the shape of the implant, and which serves to create or process the cavity 62 in the bone 60. FIG. 23C shows the joint prosthesis 10 to be implanted in the cavity 62 viewed from the side. The shaft is shaped as an irregular cone and comprises steps 13 with cutting edges 14, surface ranges 16 of a thermoplastic material situated between the cutting edges, and axially extending furrowing or tapping structures 21 (ribs).

Starting out from the bone geometry ascertained by means of CT or MRI, the joint prosthesis 10 and the processing tool 58 are selected or produced in essentially the same manner as described for the dental implant in connection with FIG. 21. Therein the implant 10 and the cavity 62 are planned such that implant anchoring by means of the cutting edges 14 and the ribs 21 is located in the epiphyseal and metaphyseal areas. The surface ranges 16 of the thermoplastic material are placed at points exposed to increased tensile and shearing stress. Therewith it becomes possible to reduce bone dislocations which are not favourable for osseointegration or to reduce to an uncritical level bone elongation in the contact area between implant and bone. In creating the cavity the first opening can be produced by standard instruments. At least for the last clearance step the processing tool 58 adapted to the shape of the implant is used in order to adjust the shape of the cavity 62 sufficiently to that of the implant 10.

Figure 24A:
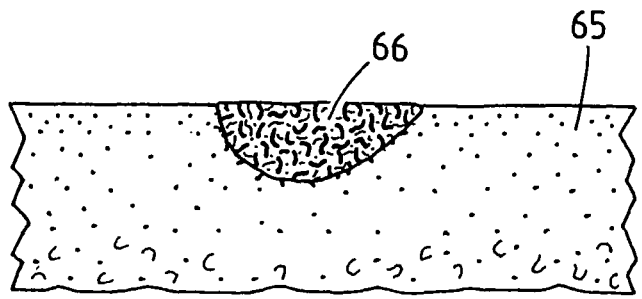
FIG. 24A to 24C illustrate the repair of an bone area damaged by a bone tumour with the aid of an implant according to the invention.
Figure 24B:
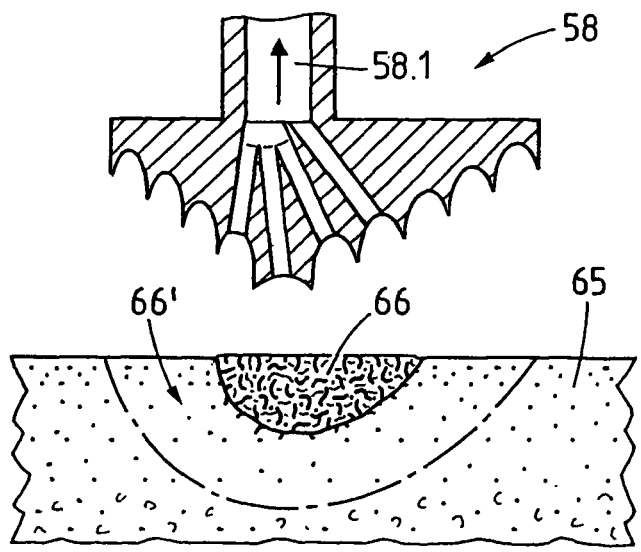
Figure 24C:
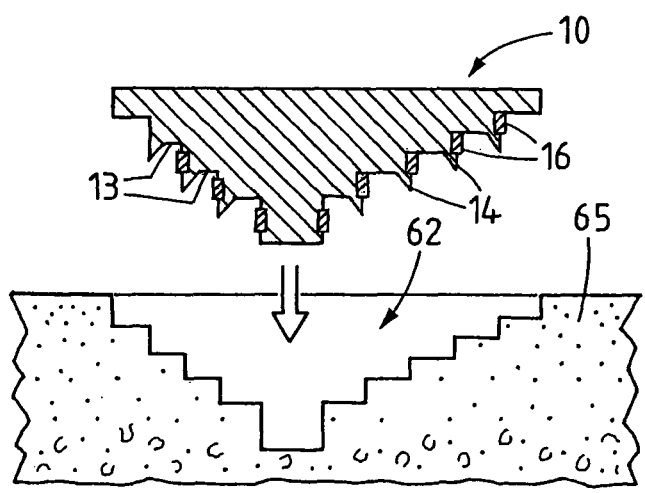

FIGS. 24A to 24C illustrate the repair of a bone defect resulting from the removal of a bone tumour with an implant according to the invention 10, which implant is to bridge the defect. FIG. 24A shows, in section, the bone 65 with the tumour 66. FIG. 24B shows, in section, the bone 66' to be removed (excision) and the processing tool 58 to be used at least for the completion of the cavity 62. FIG. 24C shows, in section, the completed cavity 62 and the implant 10 to be implanted in the cavity, which implant once again is shaped e.g. like an irregular cone comprising steps 13 with cutting edges 14 and surface ranges 16 of a thermoplastic material.

The bone tumour 66 is initially geometrically defined by X-ray, CT or MRI. Based on the measuring data the size of the excision is decided on by the surgeon. The implant 10 and the processing tool 58 are selected or specifically produced in accordance with the excision geometry.

The processing tool 58 further comprises suction channels 58.1 leading into the tool surface in the area of the cutting edges of the steps. Through these suction channels 58.1 bone material, bone marrow and tumorous cells are sucked out of the cavity, increasing the volume cleared by the tool 58, and avoiding the build-up of local pressures which could lead to fatty embolism. Sucking off the tumorous cells also prevents their transfer into healthy tissue, thus considerably reducing the risk of metastasizing cells being left behind.

The previously described Figs. and the corresponding description parts relate in most cases to specific implants (dental implant, joint prosthesis, individual implant, standard implant, etc.) and to specific characteristics of these implants. It is of course possible to apply the described characteristics to other implants and in combinations different from the ones described herein. Thus implants can be created which are not specifically described but nevertheless belong to the invention.

The invention claimed is:

1. A bone implant shaped to be implanted in an implantation direction parallel to an implant axis in a cavity surrounded by a cavity wall of bone tissue and comprising:
   an implant portion to be implanted, said implant portion having an outer surface and an inner surface, said outer surface defining depressions and chip forming cutting edges, said inner surface including energy directors and defining a hollow space that receives liquefiable material that is liquefied by mechanical oscillation, wherein openings that lead from the hollow space to the depressions are formed through the implant portion, said openings serving as passageways to direct and communicate liquefied material from the hollow space to the depressions and thereby form surface ranges at predefined locations on the outer surface of the implant portion that protrude from the depressions, and wherein the energy directors are disposed at an inlet to the openings; and wherein the chip forming cutting edges are capable of cutting the cavity wall of bone tissue, said cutting edges not extending in a common plane with the implants axis, said cutting edges facing toward a distal end region of the implant and extending at least partly around the circumference of the implant, and wherein said cutting edges are spaced from the implant axis by implants-axis-to-cutting-edges-distances, which are decreasing in the implanting direction.

2. The bone implant according to claim 1, wherein the cutting edges are designed to be salient.

3. The bone implant according to claim 1, wherein the cutting edges are undercut to form a chip space.

4. The bone implant according to claim 1, wherein a proximal end region of the implant comprises a collar with a lower edge fashioned as a cutting edge.

5. The bone implant according to claim 4, wherein the proximal end region comprises a ring of a thermoplastic material.

6. The bone implant according to claim 1, further comprising a piston, said piston being insertable into a proximal opening of the hollow space.

7. The bone implant according to claim 6, wherein, on a proximal end of the piston and/or round the proximal opening of the hollow space, an insulating connection between piston and implant is provided.

8. The bone implant according to claim 1, wherein said implant carries an intermediate element on a proximal end region.

9. The bone implant according to claim 8, wherein the intermediate element is connected to the implant by a loose fit connection and/or is equipped to be joined to a sonotrode via a loose fit connection.

10. The bone implant according to claim 1, wherein said implant is a dental implant.

11. The bone implant according to claim 10, wherein said cutting edges are comprising a wedge angle β between a proximal and a distal cutting edge surface of less than 90°.

12. The bone implant according to claim 1, wherein the implant portion to be implanted comprises at least some non-circular cross sections at a right angle to the implant.

13. A bone implant suitable for implantation in an implantation direction parallel to an implant axis in a cavity surrounded by a cavity wall of bone tissue comprising an implant portion, wherein the implant portion to be implanted comprises exterior surface ranges formed by pressing liquefiable material out of a hollow space in the implant through openings that extend through the implant portion, and wherein the implant portion further comprises energy directors at an inlet to the openings to direct liquefied material into the openings and chip forming cutting edges being disposed on an exterior of the implant portion and being capable of cutting the cavity wall of bone tissue, said cutting edges not extending in a common plane with the implant axis, said cutting edges facing toward a distal end region of the implant and extending at least partly around the circumference of the implant, wherein said cutting edges comprise a wedge angle β between a proximal and a distal cutting edge surface of less than 90°, a clearance angle α between the proximal edge surface and a cylindrical surface rotated around the implant axis with a sum of α plus β being smaller than 90°, and an angle Y between the distal cutting edge surface and the implant axis of 90° or less and wherein said cutting edges are distanced from the implant axis by implant-axis-to-cutting-edge-distances, which implant-axis-to-cutting-edge-distances are decreasing in the implanting direction.

14. A bone implant shaped to be implanted without substantial rotation in an implantation direction parallel to an implant axis into a cavity in bone tissue wherein an implant portion to be implanted comprises:
 an interior surface defining an energy director, said energy director being at an inlet to an opening extending through said implant portion;
 cutting edges and exterior surface ranges of a material which is liquefiable by mechanical vibration,
 and wherein said cutting edges:
 are not extending in a common plane with the implant axis,
 are chip forming cutting edges capable of cutting a cavity wall of bone tissue,
 are facing toward a distal end region of the implant and are extending at least partly around the circumference of the implant,
 wherein said exterior surface ranges are formed by pressing the liquefiable material out of a hollow space in the implant and through the opening to the outer surface of the implant.

15. The bone implant according to claim 14, being a dental implant.

16. The bone implant according to claim 14, the cavity in bone tissue being surrounded by a cavity wall of bone tissue.

17. The bone implant according to claim 14, wherein said cutting edges are comprising a wedge angle β between a proximal and a distal cutting edge surface of less than 90°.

18. The bone implant according to claim 14, wherein said cutting edges are distanced from the implant axis by implant-axis-to-cutting-edge-distances, which are decreasing in the implanting direction.

19. The bone implant according to claim 14, wherein said cutting edges are shaped to be reaming as they are moved into the bone tissue.

20. The bone implant according to claim 14, wherein osseointegrative surface areas are situated between the surface ranges of the liquefiable material.

21. The bone implant according to claim 14, wherein the implant portion to be implanted further comprises axially extending furrowing or tapping structures.

22. The bone implant according to claim 14, wherein the bone implant is a shaft of a joint prosthesis.

23. The bone implant according to claim 14, wherein the implant is adapted to bridge a bone defect.

24. A bone implant shaped to be implanted without substantial rotation in an implantation direction parallel to an implant axis into a cavity of bone tissue comprising:
 a root portion having the shape of an irregular cone with at least some of its cross sections not being round and/or its axis not being straight suitable for implantation in an implantation direction parallel to an implant axis in a cavity surrounded by a cavity wall of bone tissue and comprising an implant portion to be implanted,
 wherein the implant portion to be implanted comprises an interior surface defining an energy director, said energy director being at an inlet to an opening extending through said implant portion, said implant portion further comprising exterior surface ranges formed on the outer side of the implant by pressing the liquefiable material out of a hollow space in the implant through the openings to the outer surface of the implant,
 and wherein the implant portion to be implanted further comprises chip forming cutting edges capable of cutting the cavity wall of bone tissue, said cutting edges not extending in a common plane with the implant axis, and said cutting edges facing toward a distal end region of the implant and extending at least partly around the circumference of the implant.

* * * * *